United States Patent
Omr et al.

(10) Patent No.: US 10,837,794 B2
(45) Date of Patent: Nov. 17, 2020

(54) METHOD AND SYSTEM FOR CHARACTERIZATION OF ON FOOT MOTION WITH MULTIPLE SENSOR ASSEMBLIES

(71) Applicant: Invensense Inc., San Jose, CA (US)

(72) Inventors: Medhat Omr, Calgary (CA); Jacques Georgy, Calgary (CA); Aboelmagd Noureldin, Kingston (CA)

(73) Assignee: InvenSense, Inc., San Jose, CA (US)

( * ) Notice: Subject to any disclaimer, the term of this patent is extended or adjusted under 35 U.S.C. 154(b) by 737 days.

(21) Appl. No.: 14/617,743

(22) Filed: Feb. 9, 2015

(65) Prior Publication Data

US 2016/0169703 A1    Jun. 16, 2016

Related U.S. Application Data

(60) Provisional application No. 62/091,442, filed on Dec. 12, 2014.

(51) Int. Cl.
| | |
|---|---|
| G01C 22/00 | (2006.01) |
| A61B 5/00 | (2006.01) |
| A61B 5/11 | (2006.01) |
| G06F 19/00 | (2018.01) |

(52) U.S. Cl.
CPC ............ G01C 22/006 (2013.01); A61B 5/112 (2013.01); A61B 5/6801 (2013.01); G06F 19/3481 (2013.01); A61B 5/1112 (2013.01); A61B 2562/0219 (2013.01)

(58) Field of Classification Search
CPC ..... G01C 22/006; A61B 5/6801; A61B 5/112; A61B 5/1112; A61B 2562/0219; G16H 20/30; G06F 19/3481
See application file for complete search history.

(56) References Cited

U.S. PATENT DOCUMENTS

| | | | | |
|---|---|---|---|---|
| 2014/0256511 | A1* | 9/2014 | Smith | G16H 20/30 482/8 |
| 2015/0153380 | A1* | 6/2015 | Elhoushi | G01P 15/14 702/141 |
| 2015/0186944 | A1* | 7/2015 | Forsblom | G06Q 30/0252 705/14.64 |
| 2015/0362330 | A1* | 12/2015 | Omr | A61B 5/112 702/160 |
| 2016/0250094 | A1* | 9/2016 | Amundson | A61H 1/0266 623/24 |

* cited by examiner

*Primary Examiner* — Vongsavanh Sengdara
(74) *Attorney, Agent, or Firm* — Bay Area Technology Law Group

(57) ABSTRACT

Systems and methods are disclosed for characterizing on foot motion of a user with a portable device by obtaining parameters sufficient to characterize the on foot motion of the user from multiple sensor assemblies. Each additional sensor assembly may be independent of each other. The characterization of on foot motion is provided by synthesizing the parameters from the sensor assemblies. Characterization of on foot motion may include detecting a step, estimating step length, or both.

48 Claims, 9 Drawing Sheets

METHOD AND SYSTEM FOR CHARACTERIZATION OF ON FOOT MOTION WITH MULTIPLE SENSOR ASSEMBLIES

CROSS REFERENCE TO RELATED APPLICATIONS

This application claims priority from and benefit of U.S. Provisional Patent Application Ser. No. 62/091,442, filed Dec. 12, 2014, which is entitled "METHOD AND APPARATUS FOR ENHANCED STEP DETECTION AND STEP LENGTH ESTIMATION FROM MULTIPLE SENSORS ASSEMBLIES," which is assigned to the assignee hereof and is incorporated by reference in its entirety.

FIELD OF THE PRESENT DISCLOSURE

This disclosure generally relates to characterization of on foot motion and more particularly to characterization of such motion using multiple sensor assemblies.

BACKGROUND

Portable electronic devices, such as those configured to be handheld or otherwise associated with a user, are employed in a wide variety of applications and environments. The ubiquity of such devices as mobile phones, wearables, including smart watches and glasses, digital still cameras and video cameras, handheld music and media players, portable video game devices and controllers, tablets, mobile internet devices (MIDs), personal navigation devices (PNDs), and other similar devices speaks the popularity and desire for these types of devices. Increasingly, such devices are equipped with one or more sensors or other systems for determining the position or motion of the portable device. One popular application for such devices involves the characterization of on foot motion of a user. For example, motion sensor data may be processed to determine when a step of the user causes a corresponding pattern of data. In turn, the number of user steps may be used in a wide applications, including personal fitness, activity tracking, pedometer functions, navigation, dead reckoning, and the like. Further, motion sensor data may also be processed to provide an estimation of the step length of the user. As will be appreciated, this value in conjunction with the number of steps allows for greater accuracies when determining distances moved by the device.

Navigational applications may provide the user with directions, route finding, route tracking and the like or may enable location awareness so that the device provides data relevant to the geographical position of the user or otherwise customize operation of the device. Often, improved results may be obtained by combining or fusing information from multiple sources. As such, use of properly characterized on foot motion may be synthesized with other navigational techniques, including reference-based and self-contained systems. For example, reference-based strategies may include satellite-based navigation, such as a Global Navigation Satellite System (GNSS), and signal trilateration using wireless local area networks (WLANs) or cellular telecommunication systems, while self-contained strategies may include dead reckoning determinations based upon the integration of specific forces and angular rates measured by inertial sensors (e.g. accelerometer, gyroscopes) integrated into the device.

Accurate characterization of on foot motion may be used in a wide variety of other uses as well. Performance in the context of personal fitness applications, such as activity tracking or pedometer measurements, directly depends on the ability to properly correlate detected motion of the portable device with movement of the user.

Given this variety of beneficial applications, there exists a need for providing techniques to characterize on foot motion of a user. In one aspect, it would be desirable to accurately detect when and/or how many times a user steps while walking, running or undergoing similar forms of locomotion. Further, it would be desirable to estimate a distance moved corresponding to each step, or step length. It would also be desirable to implement such techniques whether the device is affixed, or strapped, to the user or not and whether the mobility of the device is constrained or unconstrained with the user. For example, the device may be oriented in any position and its orientation may vary while the user is undergoing the on foot motion being characterized. Accordingly, this disclosure satisfies these and other goals as described in the following materials.

SUMMARY

As will be described in detail below, this disclosure includes methods for characterizing on foot motion of a user with a portable device involving obtaining parameters sufficient to characterize the on foot motion of the user from a first sensor assembly integrated with the portable device, obtaining parameters sufficient to characterize the on foot motion of the user from at least one additional sensor assembly, wherein each additional sensor assembly is independent of the first sensor assembly and synthesizing the parameters obtained from the first sensor assembly and the parameters obtained from each additional sensor assembly to characterize the on foot motion of the user.

This disclosure also includes embodiments involving a portable device for characterizing on foot motion of a user having a first sensor assembly integrated with the portable device, configured to output parameters sufficient to characterize the on foot motion of the user, at least one additional sensor assembly communicably coupled to the portable device, wherein each additional sensor assembly is configured to output parameters sufficient to characterize the on foot motion of the user and is independent of the first sensor assembly and a step controller configured to synthesize the parameters output by the first sensor assembly and the parameters output by each additional sensor assembly to characterize the on foot motion of the user.

Further, this disclosure includes a system for characterizing on foot motion of a user including a first sensor assembly integrated with a first portable device, configured to output parameters sufficient to characterize the on foot motion of the user, at least one additional sensor assembly integrated with a second portable device, wherein each additional sensor assembly is configured to output parameters sufficient to characterize the on foot motion of the user and is independent of the first sensor assembly and wherein the first portable device is communicably coupled with the second portable device and a step controller implemented in at least one of the portable devices configured to synthesize the parameters output by the first sensor assembly and the parameters output by each additional sensor assembly to characterize the on foot motion of the user.

DETAILED DESCRIPTION

Figure 1A:
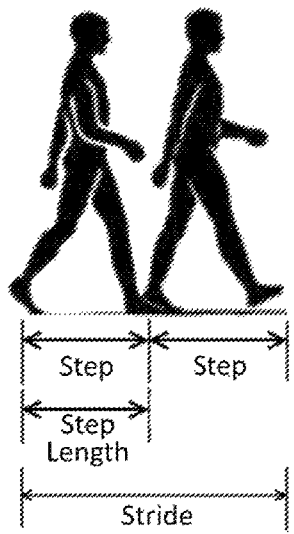
FIGS. 1A, 1B and 1C are schematic diagrams showing characteristics of on foot motion of a user, as may be determined using multiple independent sensor assemblies in one or more devices, according to an embodiment embondiments.

At the outset, it is to be understood that this disclosure is not limited to particularly exemplified materials, architectures, routines, methods or structures as such may vary. Thus, although a number of such options, similar or equivalent to those described herein, can be used in the practice or embodiments of this disclosure, the preferred materials and methods are described herein.

It is also to be understood that the terminology used herein is for the purpose of describing particular embodiments of this disclosure only and is not intended to be limiting.

The detailed description set forth below in connection with the appended drawings is intended as a description of exemplary embodiments of the present disclosure and is not intended to represent the only exemplary embodiments in which the present disclosure can be practiced. The term "exemplary" used throughout this description means "serving as an example, instance, or illustration," and should not necessarily be construed as preferred or advantageous over other exemplary embodiments. The detailed description includes specific details for the purpose of providing a thorough understanding of the exemplary embodiments of the specification. It will be apparent to those skilled in the art that the exemplary embodiments of the specification may be practiced without these specific details. In some instances, well known structures and devices are shown in block diagram form in order to avoid obscuring the novelty of the exemplary embodiments presented herein.

For purposes of convenience and clarity only, directional terms, such as top, bottom, left, right, up, down, over, above, below, beneath, rear, back, and front, may be used with respect to the accompanying drawings or chip embodiments. These and similar directional terms should not be construed to limit the scope of the disclosure in any manner.

In this specification and in the claims, it will be understood that when an element is referred to as being "connected to" or "coupled to" another element, it can be directly connected or coupled to the other element or intervening elements may be present. In contrast, when an element is referred to as being "directly connected to" or "directly coupled to" another element, there are no intervening elements present.

Some portions of the detailed descriptions which follow are presented in terms of procedures, logic blocks, processing and other symbolic representations of operations on data bits within a computer memory. These descriptions and representations are the means used by those skilled in the data processing arts to most effectively convey the substance of their work to others skilled in the art. In the present application, a procedure, logic block, process, or the like, is conceived to be a self-consistent sequence of steps or instructions leading to a desired result. The steps are those requiring physical manipulations of physical quantities. Usually, although not necessarily, these quantities take the form of electrical or magnetic signals capable of being stored, transferred, combined, compared, and otherwise manipulated in a computer system.

It should be borne in mind, however, that all of these and similar terms are to be associated with the appropriate physical quantities and are merely convenient labels applied to these quantities. Unless specifically stated otherwise as apparent from the following discussions, it is appreciated that throughout the present application, discussions utilizing the terms such as "accessing," "receiving," "sending," "using," "selecting," "determining," "normalizing," "multiplying," "averaging," "monitoring," "comparing," "applying," "updating," "measuring," "deriving" or the like, refer to the actions and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Embodiments described herein may be discussed in the general context of processor-executable instructions residing on some form of non-transitory processor-readable medium, such as program modules, executed by one or more computers or other devices. Generally, program modules include routines, programs, objects, components, data structures, etc., that perform particular tasks or implement particular abstract data types. The functionality of the program modules may be combined or distributed as desired in various embodiments.

In the figures, a single block may be described as performing a function or functions; however, in actual practice, the function or functions performed by that block may be performed in a single component or across multiple components, and/or may be performed using hardware, using software, or using a combination of hardware and software. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure. Also, the exemplary wireless communications devices may include components other than those shown, including well-known components such as a processor, memory and the like.

The techniques described herein may be implemented in hardware, software, firmware, or any combination thereof, unless specifically described as being implemented in a specific manner. Any features described as modules or components may also be implemented together in an integrated logic device or separately as discrete but interoperable logic devices. If implemented in software, the techniques may be realized at least in part by a non-transitory processor-readable storage medium comprising instructions that, when executed, performs one or more of the methods described above. The non-transitory processor-readable data storage medium may form part of a computer program product, which may include packaging materials.

The non-transitory processor-readable storage medium may comprise random access memory (RAM) such as synchronous dynamic random access memory (SDRAM), read only memory (ROM), non-volatile random access memory (NVRAM), electrically erasable programmable read-only memory (EEPROM), FLASH memory, other known storage media, and the like. The techniques additionally, or alternatively, may be realized at least in part by a processor-readable communication medium that carries or communicates code in the form of instructions or data structures and that can be accessed, read, and/or executed by a computer or other processor. For example, a carrier wave may be employed to carry computer-readable electronic data such as those used in transmitting and receiving electronic mail or in accessing a network such as the Internet or a local area network (LAN). Of course, many modifications may be made to this configuration without departing from the scope or spirit of the claimed subject matter.

The various illustrative logical blocks, modules, circuits and instructions described in connection with the embodiments disclosed herein may be executed by one or more processors, such as one or more motion processing units (MPUs), digital signal processors (DSPs), general purpose microprocessors, application specific integrated circuits (ASICs), application specific instruction set processors (ASIPs), field programmable gate arrays (FPGAs), or other equivalent integrated or discrete logic circuitry. The term "processor," as used herein may refer to any of the foregoing structure or any other structure suitable for implementation of the techniques described herein. In addition, in some aspects, the functionality described herein may be provided within dedicated software modules or hardware modules configured as described herein. Also, the techniques could be fully implemented in one or more circuits or logic elements. A general purpose processor may be a microprocessor, but in the alternative, the processor may be any conventional processor, controller, microcontroller, or state machine. A processor may also be implemented as a combination of computing devices, e.g., a combination of an MPU and a microprocessor, a plurality of microprocessors, one or more microprocessors in conjunction with an MPU core, or any other such configuration.

Unless defined otherwise, all technical and scientific terms used herein have the same meaning as commonly understood by one having ordinary skill in the art to which the disclosure pertains.

Finally, as used in this specification and the appended claims, the singular forms "a, "an" and "the" include plural referents unless the content clearly dictates otherwise.

As noted above, multiple uses exist for a mobile device having the ability to characterize on foot motion of a user, such as by detecting a user's steps and/or estimating the length of each step. Such applications include, without limitation, personal fitness, activity tracking, pedometer functions, navigation, and dead reckoning. For example, navigation applications using mobile/smart phones are becoming very popular as they come equipped with Assisted Global Positioning System (AGPS) chipsets to be used with a Global Navigation Satellite System (GNSS) and further use high sensitivity capabilities to provide absolute positions or orientations of the platform (e.g. user) even in some environments that cannot guarantee clear line of sight to satellite signals. In some circumstances, such as deep indoor environments or challenging outdoor environments, navigation or localization may incorporate cell tower ID or, if possible, cell tower trilateration for a position fix where AGPS solution is unavailable. Despite these two positioning methods that already come in many mobile devices, accurate indoor localization still presents a challenge and fails to satisfy the accuracy demands of today's location based services (LBS). Additionally, these methods may only provide the absolute heading of the platform without any information on the device's heading.

Many mobile devices, such as mobile phones, tablets, smart watches, smart glasses, belt clips and other APPlication acCESSORIES (or Appcessories for short), are equipped with Micro Electro Mechanical System (MEMS) sensors that are used predominantly for screen control and entertainment applications. These sensors have not been broadly used to date for navigation purposes due to very high noise, large random drift rates, and frequently changing orientations with respect to the carrying platform or person. Magnetometers are also found within many mobile devices. In some cases, it has been shown that a navigation solution using accelerometers and magnetometers may be possible if the user is careful enough to keep the device in a specific orientation with respect to their body, such as when held carefully in front of the user after calibrating the magnetometer.

As such, there is a need for a navigation solution capable of accurately utilizing measurements from a device within a platform to determine the navigation state of the device/platform without any constraints on the platform (i.e. in indoor or outdoor environments) or the mobility of the device. It is further desirable that the estimation of the position and attitude of the platform be independent of the usage of the device (e.g. the way the user is holding or moving the device during navigation).

In addition to the above mentioned application of portable devices, such as for example smart phones and tablets, (that may involve a full navigation solution including position, velocity and attitude, or position and attitude), there are other applications (that may involve estimating a full navigation solution, or an attitude only solution or an attitude and velocity solution) where the method to mitigate the aforementioned problems is needed for enhancing the user experience and usability, and may be applicable in a number of scenarios, including the non-limiting examples of video gaming equipment, augmented reality equipment, wearable computing devices (such as for example smart wrist watches, and smart glasses) and other appcessories.

The main challenge is that the low-cost MEMS sensors in current wearable computing devices, appeessories, or even portable devices are considered insufficient for reliable navigation purposes due to very high noise, large random drift rates, and especially for such mobile devices that can freely change orientation with respect to the platform or person. Some prior solutions to overcome such limitations of the sensors errors is through better error modeling, however this is challenging for portable navigation which must accommodate varying orientation with respect to the platform or person.

Figure 2:
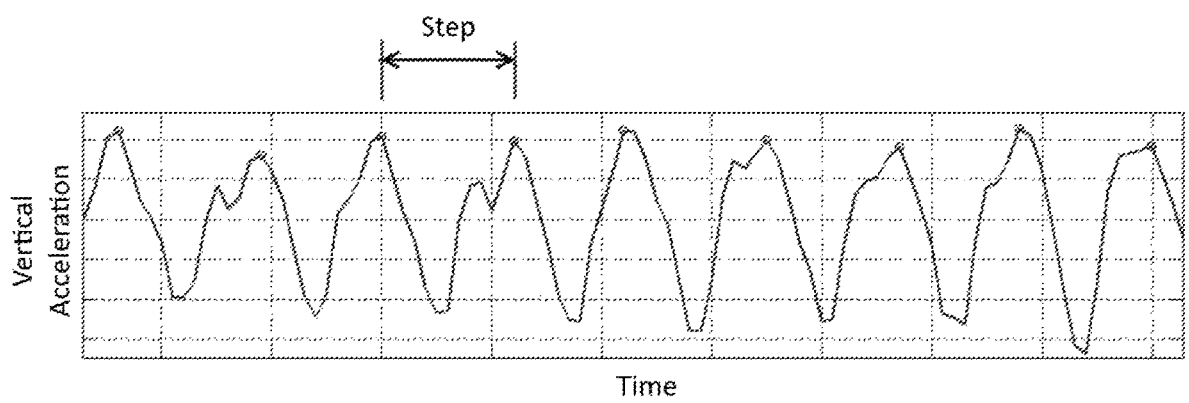
FIG. 2 illustrates inertial sensor data that may be used for characterizing on foot motion according to an embodiment.

Inertial sensors (e.g. accelerometers and gyroscopes) may be used for tracking human movements, especially "on foot" activities (such as walking, running or other foot-based forms of locomotion) in the context of this disclosure. In one aspect, data from an accelerometer may be used to detect steps and to which step length estimation techniques may be applied. As shown in FIG. 1A, each step of a user begins on one foot and ends on the opposite foot. Correspondingly, two successive steps, may be defined as the user's stride. Step length may refer to the distance associated with each step as illustrated. The vertical acceleration of the user may be sampled over time as shown in FIG. 2, such that detected peaks in the measured vertical acceleration may be correlated to steps.

Conventionally, techniques for characterizing the on foot motion of a user have relied on the use of a single sensor assembly, such as with a pedometer. As will be described below, aspects of this disclosure provide enhanced characterization of on foot motion by using two or more independent sensor assemblies. In general, one or more devices may be held by, carried by, affixed to, secured to or otherwise associated with a user such that on foot motion of the user results in a corresponding motion of the one or more devices. Each device may be implemented as a construct that may be moved in space by a user and its motion, location and/or orientation in space therefore sensed using at least one associated sensor assembly. For example, such a handheld device may be a mobile phone (e.g., cellular phone, a phone running on a local network, or any other telephone handset), wired telephone (e.g., a phone attached by a wire), personal digital assistant (PDA), video game player, video game controller, navigation device, activity or fitness tracker device (e.g., bracelet or clip), smart watch, glasses, other wearable device, mobile internet device (MID), personal navigation device (PND), digital still camera, digital video camera, binoculars, telephoto lens, portable music, video, or media player, remote control, or other handheld device, or a combination of one or more of these devices. In some cases, the design of the device may determine how the device is typically associated with a user, such as a watch that may be affixed to the wrist or glasses that may be worn. Other devices may be associated with a user in multiple ways, such as a phone that may be carried in the hand or secured in a pocket and may also be used in varying contexts or orientations depending on use case, including relatively horizontal in a texting mode, relatively vertical when on ear in a calling mode or dangling when being carried but not actively used.

Figure 3:
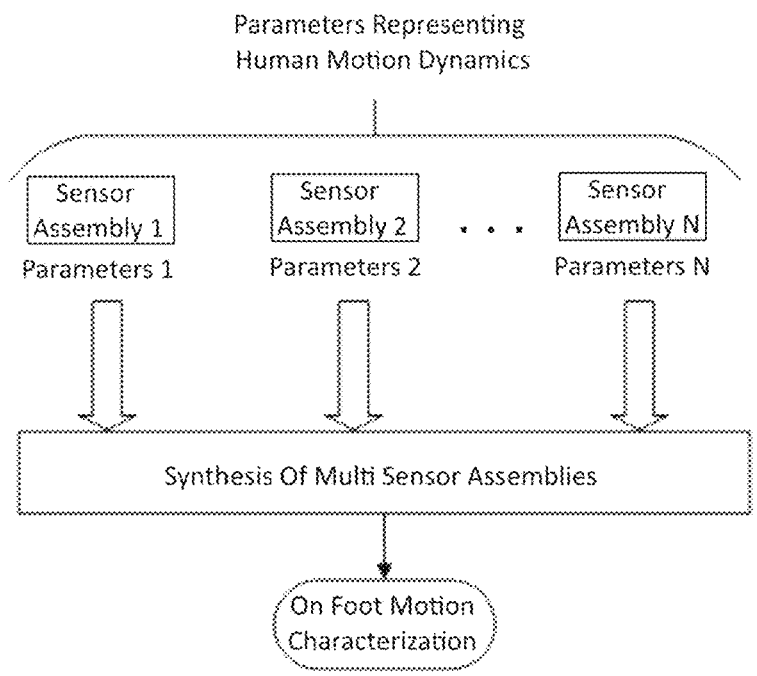
FIG. 3 is a schematic representation of synthesizing parameters from multiples sensor assemblies to characterize on foot motion according to an embodiment.

A plurality of such devices may be employed in practicing the techniques of this disclosure, such that each device includes one or more independent sensor assemblies, or a single device may include a plurality of independent sensor assemblies. Thus, during on foot motion, the sensor assemblies of the device(s) may generate parameters and other data used to characterize that motion. As shown in FIG. 3, each sensor assembly may independently measure one or more parameters that may be used to characterize on foot motion of the user. The output of each sensor assembly is synthesized to produce the final on foot motion of characterization. A number of suitable architectures may be employed, ranging from each sensor assembly characterizing the on foot motion independently and combining the independent characterizations to combining the parameters and performing a single characterization of on foot motion using the combined parameters. As will be appreciated, any intermediate level of architecture may also be employed, such that some parameters are combined before performing a characterization for each sensor assembly followed by combining the separate characterizations.

Figure 1B:
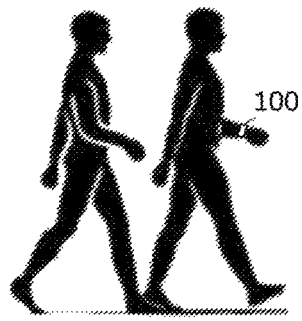
Figure 1C:
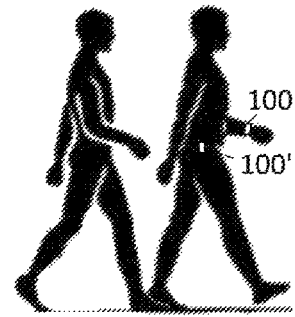
Figure 4:
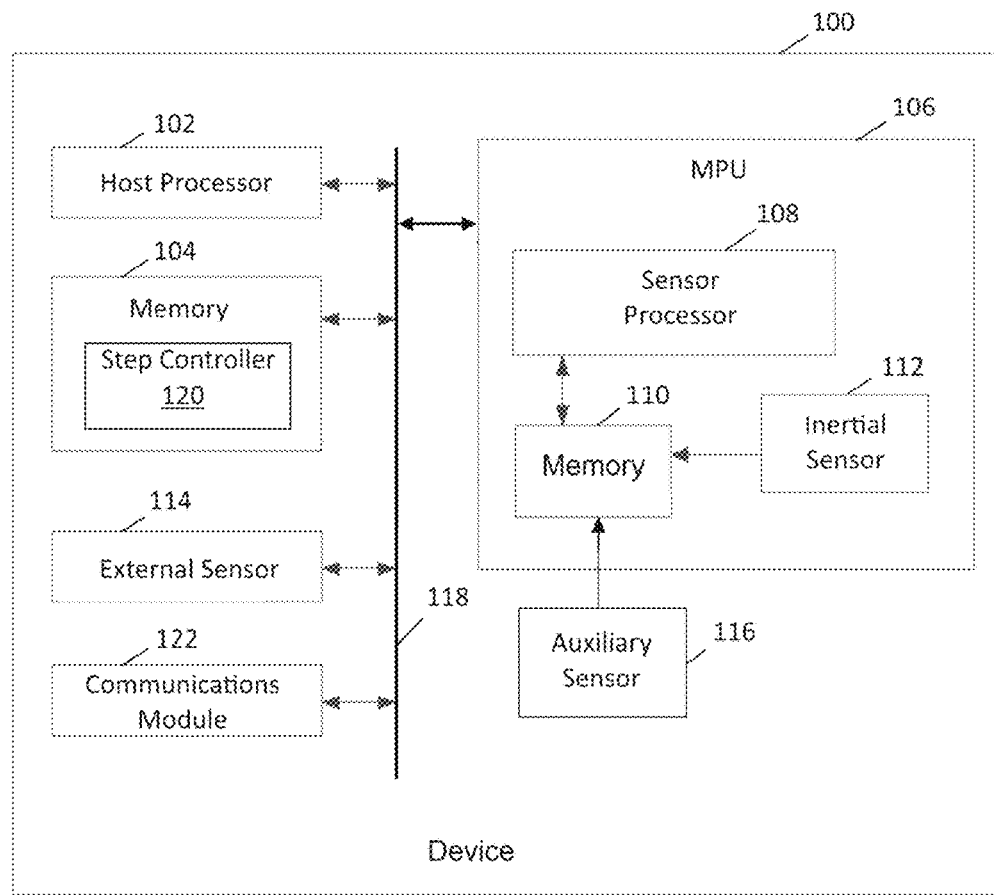
FIG. 4 is a schematic diagram of a device for characterizing on foot motion using multiple sensor assemblies according to an embodiment.

These and other aspects of this disclosure may be appreciated in the context of FIG. 4, which depicts features of a suitable portable device 100 with high level schematic blocks. Either a single device 100 having multiple sensor assemblies, as shown in FIG. 1B, or multiple devices 100 and 100' each having at least one sensor assembly, may be used, as shown in FIG. 1C. As shown, device 100 includes a host processor 102, which may be one or more microprocessors, central processing units (CPUs), or other processors to run software programs, which may be stored in memory 104, associated with the functions of device 100. Multiple layers of software can be provided in memory 104, which may be any combination of computer readable medium such as electronic memory or other storage medium such as hard disk, optical disk, etc., for use with the host processor 102. For example, an operating system layer can be provided for device 100 to control and manage system resources in real time, enable functions of application software and other layers, and interface application programs with other software and functions of device 100. Similarly, different software application programs such as menu navigation software, games, camera function control, navigation software, communications software, such as telephony or wireless local area network (WLAN) software, or any of a wide variety of other software and functional interfaces can be provided. In some embodiments, multiple different applications can be provided on a single device 100, and in some of those embodiments, multiple applications can run simultaneously.

Device 100 includes at least one sensor assembly, as shown here in the form of integrated motion processing unit (MPU™) 106 featuring sensor processor 108, memory 110 and inertial sensor 112. Memory 110 may store algorithms, routines or other instructions for processing data output by inertial sensor 112 and/or other sensors as described below using logic or controllers of sensor processor 108, as well as storing raw data and/or motion data output by inertial sensor 112 or other sensors. Inertial sensor 112 may be one or more sensors for measuring motion of device 100 in space. Depending on the configuration, MPU 106 measures one or more axes of rotation and/or one or more axes of acceleration of the device. In one embodiment, inertial sensor 112 may include rotational motion sensors or linear motion sensors. For example, the rotational motion sensors may be gyroscopes to measure angular velocity along one or more orthogonal axes and the linear motion sensors may be accelerometers to measure linear acceleration along one or more orthogonal axes. In one aspect, three gyroscopes and three accelerometers may be employed, such that a sensor fusion operation performed by sensor processor 108, or other processing resources of device 100, combines data from inertial sensor 112 to provide a six axis determination of motion. As desired, inertial sensor 112 may be implemented using MEMS to be integrated with MPU 106 in a single package. Exemplary details regarding suitable configurations of host processor 102 and MPU 106 may be found in co-pending, commonly owned U.S. patent application Ser. No. 11/774,488, filed Jul. 6, 1007, and Ser. No. 12/106,921, filed Apr. 11, 1008, which are hereby incorporated by reference in their entirety. Suitable implementations for MPU 106 in device 100 are available from InvenSense, Inc. of Sunnyvale, Calif.

Alternatively, or in addition, device 100 may implement a sensor assembly in the form of external sensor 114. External sensor may represent one or more sensors as described above, such as an accelerometer and/or a gyroscope, that measures parameters for characterizing on foot motion. As used herein, "external" means a sensor that is not integrated with MPU 106 and may be remote or local to device 100. Also alternatively or in addition, MPU 106 may receive data from an auxiliary sensor 116 configured to measure one or more aspects about the environment surrounding device 100. For example, a barometer and/or a magnetometer may be used to refine position determinations made using inertial sensor 112. In one embodiment, auxiliary sensor 116 may include a magnetometer measuring along three orthogonal axes and output data to be fused with the gyroscope and accelerometer inertial sensor data to provide a nine axis determination of motion. In another embodiment, auxiliary sensor 116 may also include a barometer to provide an altitude determination that may be fused with the other sensor data to provide a ten axis determination of motion. Although described in the context of one or more sensors being MEMS based, the techniques of this disclosure may be applied to any sensor design or implementation.

In the embodiment shown, host processor 102, memory 104. MPU 106 and other components of device 100 may be coupled through bus 118, which may be any suitable bus or interface, such as a peripheral component interconnect express (PCIe) bus, a universal serial bus (USB), a universal asynchronous receiver/transmitter (UART) serial bus, a suitable advanced microcontroller bus architecture (AMBA) interface, an Inter-Integrated Circuit (I2C) bus, a serial digital input output (SDIO) bus, a serial peripheral interface (SPI) or other equivalent. Depending on the architecture, different bus configurations may be employed as desired. For example, additional buses may be used to couple the various components of device 100, such as by using a dedicated bus between host processor 102 and memory 104.

In one aspect, the various operations of this disclosure used to characterize on foot motion may be implemented through step controller 120 as a set of suitable instructions stored in memory 104 that may be read and executed by host processor 102. Other embodiments may feature any desired division of processing between host processor 102. MPU 106 and other resources provided by device 100, or may be implemented using any desired combination of software, hardware and firmware. Multiple layers of software may be employed as desired and stored in any combination of memory 104, memory 110, or other suitable location. For example, a motion algorithm layer can provide motion algorithms that provide lower-level processing for raw sensor data provided from the motion sensors and other sensors. A sensor device driver layer may provide a software interface to the hardware sensors of device 100. Further, a suitable application program interface (API) may be provided to facilitate communication between host processor 102 and MPU 106, for example, to transmit desired sensor processing tasks. As such, aspects implemented in software may include but are not limited to, application software, firmware, resident software, microcode, etc, and may take the form of a computer program product accessible from a computer-usable or computer-readable medium providing program code for use by or in connection with a computer or any instruction execution system, such as host processor 102, sensor processor 108, a dedicated processor or any other processing resources of device 100.

Device 100 may also include communications module 122 configured to employ any suitable wired or wireless communication protocol. Communications module 122 may be used to transmit and/or receive information from other devices having independent sensor assemblies. Depending on the architecture employed, communications module may be configured to exchange information regarding parameters used to characterize on foot motion, the characterizations themselves or any suitable combination. For example, wireless protocols including cellular-based and wireless local area network (WLAN) technologies such as Universal Terrestrial Radio Access (UTRA), Code Division Multiple Access (CDMA) networks, Global System for Mobile Communications (GSM), the Institute of Electrical and Electronics Engineers (IEEE) 802.16 (WiMAX), Long Term Evolution (LTE), IEEE 802.11 (WiFi™), BLUETOOTH®, ZigBee®, ANT, near field communication (NFC), infrared (IR) and the like may be used in an embodiment.

As described above, the present disclosure relates to techniques for characterizing on foot user motion. In one aspect, this may include detecting one or more steps. In another aspect, this may include estimating step length, which may be used as a static or dynamic variable as desired. The characterization of on foot motion involves multiple sensors assemblies that need not be integrated into one device.

In one embodiment, the characterization of on foot motion may utilize measurements (readings) from sensors (such as for example, accelerometers, gyroscopes, magnetometers, etc.) whether in the presence or in the absence of additional sources of navigational information, such as satellite navigation or wireless signal positioning. In another embodiment, the characterization of on foot motion may be used for a navigation solution utilizing measurements (readings) from sensors (such as for example, accelerometers, gyroscopes, magnetometers, etc.) whether in the presence or in the absence of additional sources of navigational information In one aspect, the techniques of this disclosure may include characterizing the on foot motion of the user by detecting a step.

In one aspect, the techniques of this disclosure may include characterizing the on foot motion of the user by determining whether a step has occurred for each sensor assembly, using at least one parameter obtained from each sensor assembly in making the determination for that sensor assembly and detecting a step by comparing the determinations from each sensor assembly.

In one aspect, the techniques of this disclosure may include comparing the determinations by detecting a step when a number of determinations detecting a step exceed a number of determinations not detecting a step.

In one aspect, the techniques of this disclosure may include comparing the determinations by weighting at least one of the determinations.

In one aspect, the techniques of this disclosure may include characterizing the on foot motion of the user by estimating step length.

In one aspect, the techniques of this disclosure may include synthesizing the parameters obtained from the first sensor assembly and the parameters obtained from each additional sensor assembly by characterizing the on foot motion of the user with the parameters from the first sensor assembly, for each additional sensor assembly, characterizing the on foot motion of the user with the parameters from each additional sensor assembly and combining each characterization.

In one aspect, the techniques of this disclosure may include synthesizing the parameters obtained from the first sensor assembly and the parameters obtained from each additional sensor assembly by generating a combined parameter from at least one parameter obtained from one sensor assembly and at least one corresponding parameter obtained from another sensor assembly prior to characterizing the on foot motion using the combined parameter.

In one aspect, the techniques of this disclosure may include synthesizing the parameters obtained from the first sensor assembly and the parameters obtained from each additional sensor assembly by generating combined parameters for each of the parameters obtained from the first sensor assembly with each of the corresponding parameters obtained from at least one additional sensor assembly and characterizing the on foot motion of the user with the combined parameters.

In one aspect, the techniques of this disclosure may include characterizing the on foot motion of the user with the combined parameter and at least one parameter from one of the sensor assemblies, characterizing the on foot motion of the user with at least one parameter from another of the sensor assemblies and combining each characterization.

In one aspect, the techniques of this disclosure may include synthesizing the parameters obtained from the first sensor assembly and the parameters obtained from each additional sensor assembly by collecting the parameters from the first sensor assembly and the parameters from each additional sensor assembly and characterizing the on foot motion of the user with the collected parameters.

In one aspect, the techniques of this disclosure may include combining using an averaging operation.

In one aspect, the averaging operation may be weighted averaging

In one aspect, the techniques of this disclosure may include using the averaging operation by a dynamically adjusting a weight of at least one factor used in the averaging operation.

In one aspect, the techniques of this disclosure may involve scoring.

In one aspect, the techniques of this disclosure may include characterizing the on foot motion of the user by employing a nonlinear model.

In one aspect, the nonlinear model may be generated by performing a fast orthogonal search.

In one aspect, the techniques of this disclosure may include performing a fast orthogonal search operation by building at least one model for estimating step length using parameters corresponding to the parameters obtained from the first sensor assembly and obtained from each additional sensor assembly.

In one aspect, the techniques of this disclosure may include characterizing the on foot motion of the user by feeding the parameters obtained from the first sensor assembly and obtained from each additional sensor assembly to the at least one model to estimate step length.

In one aspect, the techniques of this disclosure may include performing a fast orthogonal search operations by building a plurality of models for characterizing the on foot motion of the user.

In one aspect, the techniques of this disclosure may include characterizing the on foot motion of the user by feeding the parameters obtained from the first sensor assembly and obtained from each additional sensor assembly to at least one model selected from a plurality of models to estimate step length.

In one aspect, the techniques of this disclosure may include classifying an activity of the user and selecting among the plurality of models based, at least in part, on the classification.

In one aspect, the techniques of this disclosure may include classifying dynamics of the user and selecting among the plurality of models based, at least in part, on the classification.

As noted, the techniques of this disclosure may include a portable device for characterizing on foot motion using multiple sensor assemblies.

In one aspect, the at least one additional sensor assembly may be integrated into the portable device.

In one aspect, the at least one additional sensor assembly may be integrated into another portable device.

In one aspect, the portable device may include a communications module configured to communicate with the other portable device.

In one aspect, the portable device may be configured as a wearable device.

In one aspect, the other portable device may be configured as a wearable device.

In one aspect, the first sensor assembly may include an inertial sensor implemented as a Micro Electro Mechanical System (MEMS).

EXAMPLES

Figure 5:
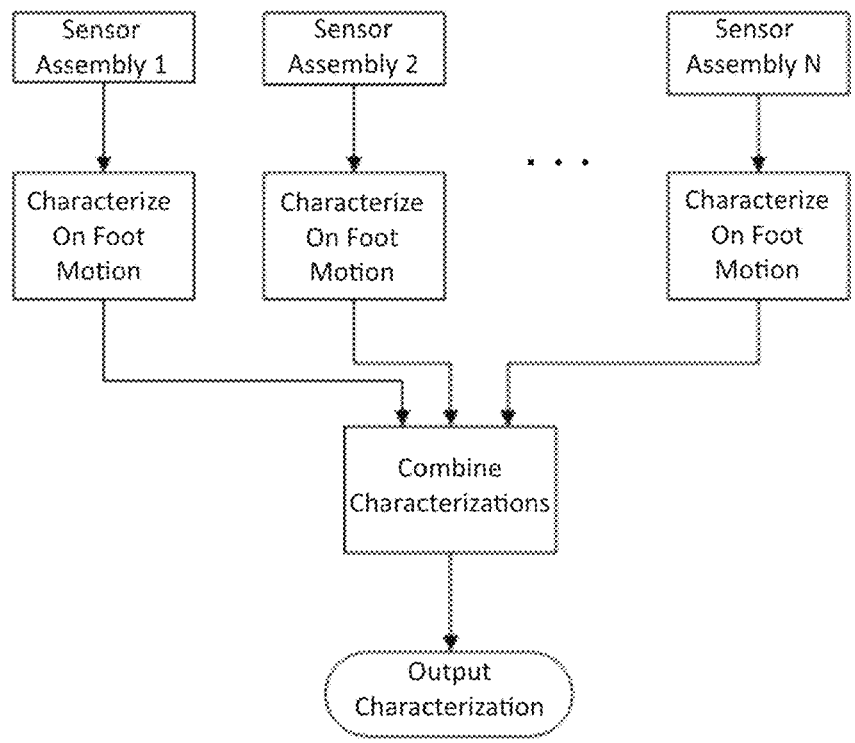
FIG. 5 is a schematic representation of an architecture for synthesizing parameters from multiples sensor assemblies to characterize on foot motion according to an embodiment.

As one example, synthesis of multiple sensor assemblies may include the parameters measured by each sensor assembly being used to independently characterize on foot motion, followed by a fusion or other combination of the independent characterizations to output a finalized characterization as illustrated in FIG. 5. This architecture is straightforward to implement and does not require that each sensor assembly be on same device or measure parameters in a similar way. In one embodiment, each sensor assembly may be associated with the user in different manners, such as illustrated by a first sensor assembly in a watch, or other similar device that is affixed to the user, and a second sensor assembly in a phone or the like that is carried by the user. Depending on the manner in which the device is associated with the user, even if the sensor assemblies employ equivalent sensors, the measurements may vary. For example, glasses worn on a user's face may experience different motion than a watch secured to a wrist. By first independently characterizing the on foot motion with each sensor assembly before fusing them, it may not be necessary to account for such differences in measurement.

Figure 6:
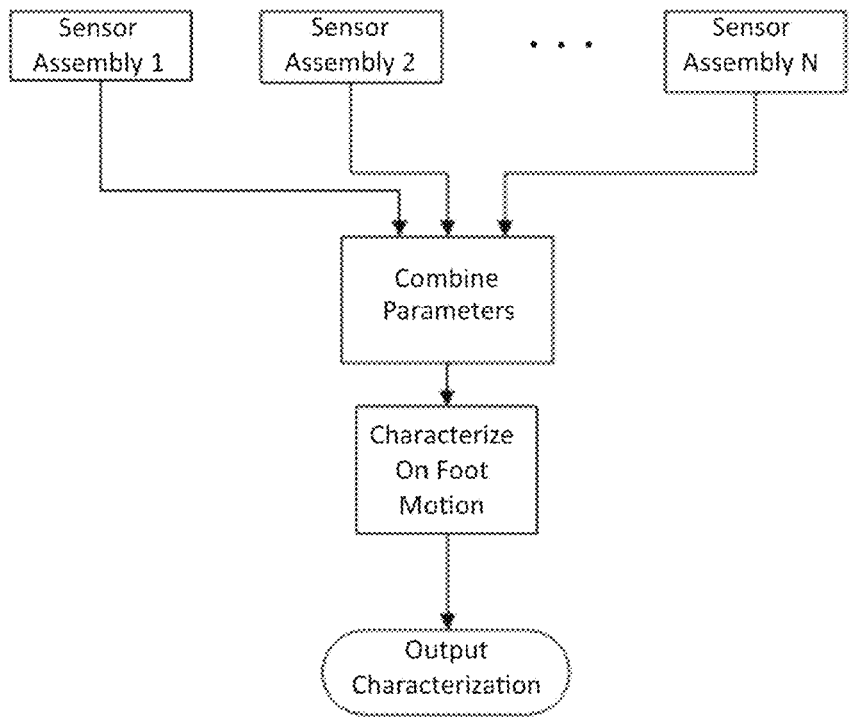
FIG. 6 is a schematic representation of another architecture for synthesizing parameters from multiples sensor assemblies to characterize on foot motion according to an embodiment.

In another example, the parameters from each sensor assembly may be combined before characterizing on foot motion, such that a single characterization operation may be performed on the combined parameters as shown in FIG. 6. Fusion of the parameters may be performed in any suitable manner, including taking a simple or weighted average. It may be advantageous to employ this architecture when the different sensor assemblies are carried on the same device or when the different sensor assemblies are on different devices but are expected to have similar measurements. In one aspect, the algorithm or model used to characterize on foot motion may be the same, regardless of whether and from how many different sensor assemblies are combined. As such, this technique may be suitable when availability of data from some of the sensor assemblies is intermittent.

Figure 7:
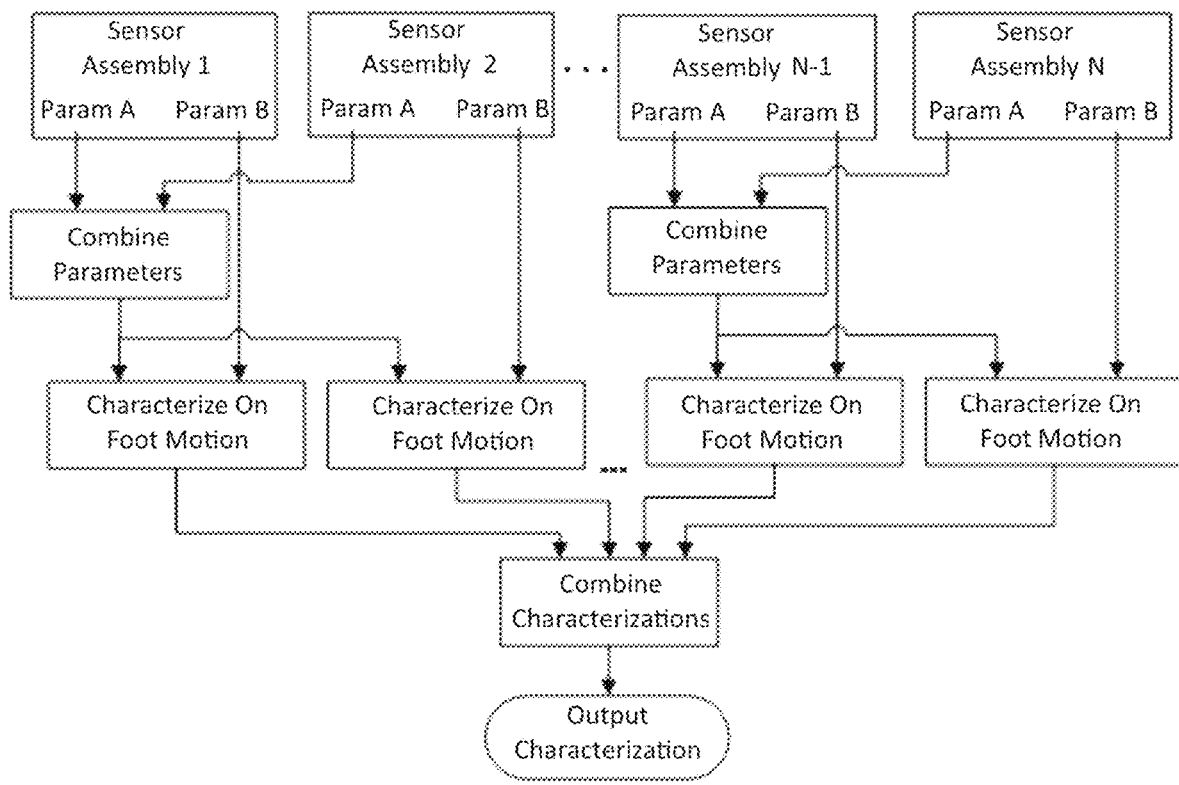
FIG. 7 is a schematic representation of yet another architecture for synthesizing parameters from multiples sensor assemblies to characterize on foot motion according to an embodiment.

In yet another example, a multi-level fusion architecture may be employed in which similar inputs coming from different sensor assemblies may be grouped and fused together so that an on foot motion characterization may be performed for each sensor assembly using both the fused parameter(s) and parameter(s) obtained directly from the sensor assembly. Subsequently, a fusion or other combination of the independent characterizations may be performed to output a finalized characterization. As shown in FIG. 7, one parameter (Param A) may be combined and then used with a directly obtained parameter (Param B) in order to generate separate characterizations corresponding to each sensor assembly which are then combined to output a final characterization. Although shown as two pairs of sensors combining the same parameter, any number and combination of parameters may be employed as warranted. As will be appreciated, it may be desirable to combine parameters expected to have similar measurements. To illustrate, step frequency exemplifies one parameter that may be combined, as it would not be expected for the user to have different step frequencies, regardless of where or how the sensor assembly is associated. On the other hand, an example of a parameter that may be used directly to generate each characterization is acceleration variance, since an accelerometer attached to a limb may be expected to exhibit a higher variance signal than a sensor assembly attached to the head or core of the user.

Figure 8:
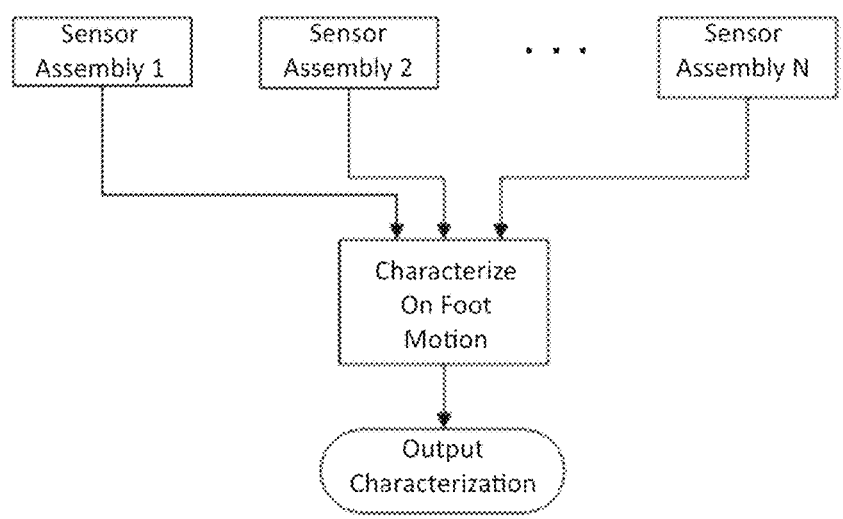
FIG. 8 is a schematic representation of still another architecture for synthesizing parameters from multiples sensor assemblies to characterize on foot motion according to an embodiment.

In still another example, parameters output by each of the sensor assemblies may be fed to a single location so that a single characterization of on foot motion may be performed as shown in FIG. 8. As such, a centralized filter may be employed to process the parameters, where all inputs coming from different sensor assemblies are used to provide the characterization of on foot motion. In one aspect, this may include tailoring the filter to accommodate differences between the parameters provided by the separate sensor assemblies. Further, characterization of on foot motion using the directly provided parameters may also incorporate any relation between two or more sensor assemblies as might be derived from a relation between the sensor assemblies measurements and/or any other statistic about these parameters, such as mean or variance.

It will be appreciated that in some embodiments, the multiple sensor assemblies may be distributed across multiple devices. As desired, any of the operations associated with the combination of parameters and/or characterizations according to the exemplary architectures described above may be performed by one or more of the devices. For example, step controller 120 of one device may receive parameters from all the sensor assemblies. Alternatively, some operations may be performed at each sensor assembly before being passed to step controller 120. Likewise, any or all of the operations may be duplicated at some or all of the devices.

In all of these architectures, the final output characterization of on foot motion may be fed back to each sensor assembly to be used as desired. For example, the output of each sensor assembly may be used by different applications, and in some embodiments, may be on different devices. By feeding back the enhanced characterization information, each sensor assembly may provide that information in a seamless manner. As another example, each sensor assembly may employ training routines or the like such that the enhanced characterization obtained from multiple sensor assemblies may be used to improve future performance of the individual sensor assemblies.

In another aspect, synthesizing parameters from multiple sensor assemblies may include enhancing a determination of step frequency. For example, an inverse function may be applied to calculate the step frequency given the enhanced step length calculated using one of the previous architectures (or method(s)). This more accurate step frequency can be used later on in the calculation of the next step length estimate.

As described above, the techniques of this disclosure may include combination or fusion of parameters and/or characterizations. These operations may be performed in any suitable manner, including taking an average of the independent characterizations. A simple average may be applied as warranted, such as when there is insufficient information about the accuracy of each sensor assembly and/or the separate characterizations associated with each sensor assembly. Correspondingly, if there is information about the accuracy (such as a priori or predefined weights depending on sensor/device type and/or position and orientation relative to the user), a weighted average may be applied. Alternatively, any machine learning or system identification driven model, such as artificial neural network, may be employed as desired.

In one aspect, a suitable technique for weighting parameters and/or characterizations prior to combination may include the use of static weights. For example, the output of one or more sensor assemblies may have hard coded weights based, at least in part, on the type of device 100 and may further represent different usage modes or expected orientations of the device, so that appropriate weights are selected for a current configuration of sensor assemblies. Similarly, a look up table may be employed to identify appropriate weights dependent on device type, usage and/or current orientation(s). Advantageously, such techniques represent computationally efficient weighting techniques.

In another aspect, a suitable technique for weighting parameters and/or characterizations prior to combination may include a scoring system. Scoring may be applied individually for each sensor assembly and/or device and usage case or orientation alone. When combined, the individual scores may be summed so that each score divided by the total sum is used as the weight of the corresponding sensor assembly when outputting the final characterization of on foot motion.

The noted scoring technique may be employed even when all possible combinations of potential participating devices and associated usage modes and/or orientations are not known. Accordingly, scores may be provided where available or may be determined and default value(s) employed for the remainder. Further, scoring may accommodate a dynamic weighting technique to allow for training of one or more devices and/or sensor assemblies. For example, when a reference for step length is available, such as from a satellite navigation solution, the score of a given device and/or sensor assembly may be adjusted to reflect the degree to which its step length estimate matches the reference. Other suitable means of validating or assigning confidence levels to a given device and/or sensor assembly may also be used.

Further, it will be appreciated that these techniques may be applied to any aspect associated with characterizing on foot motion. For example, a single sensor assembly may be used to detect steps and multiple sensor assemblies may be used to estimate step length or vice versa. In one aspect, these or other suitable architectures for synthesizing parameters from multiple sensor assemblies for step detection may be enhanced through a voting process, so that detection of a step in relation to a sufficient number of sensor assemblies may be used to impute a corresponding step detection in one or more additional sensor assemblies. As an illustration, in a set of three sensor assemblies, when a step is detected in relation to two of the assemblies, the third assembly may be treated as having detected a step. As desired, a simple or greater majority may be employed. Alternatively or in addition, one or more of the sensor assemblies may be weighted according to a confidence level to resolve ties or to override characterizations generated using sensor assemblies having a lower confidence.

In another aspect, synthesizing parameters from multiple sensor assemblies may include providing an estimation of step length. Any desired technique for estimating step length from the parameters provided by the multiple sensor assemblies may be employed, including the following representative embodiment.

Estimating step length example may assume a nonlinear relation between step length and different parameters that represent human motion dynamics such as step frequency, acceleration variance during step, acceleration peak value during step, peak to peak acceleration value during step and others. As described above, inertial sensor 112 and/or external sensor 114 may be employed to measure such parameters. Implementation of this technique may involve two phases. First, a model building phase may be prior to implementation in device 100) using an appropriate nonlinear system identification technique. In one aspect, the nonlinear system identification technique may be fed different parameters that represent human motion dynamics during on foot motion with different speeds, collected by different people with different characteristics such as weights, heights, genders, and the like.

Figure 9:
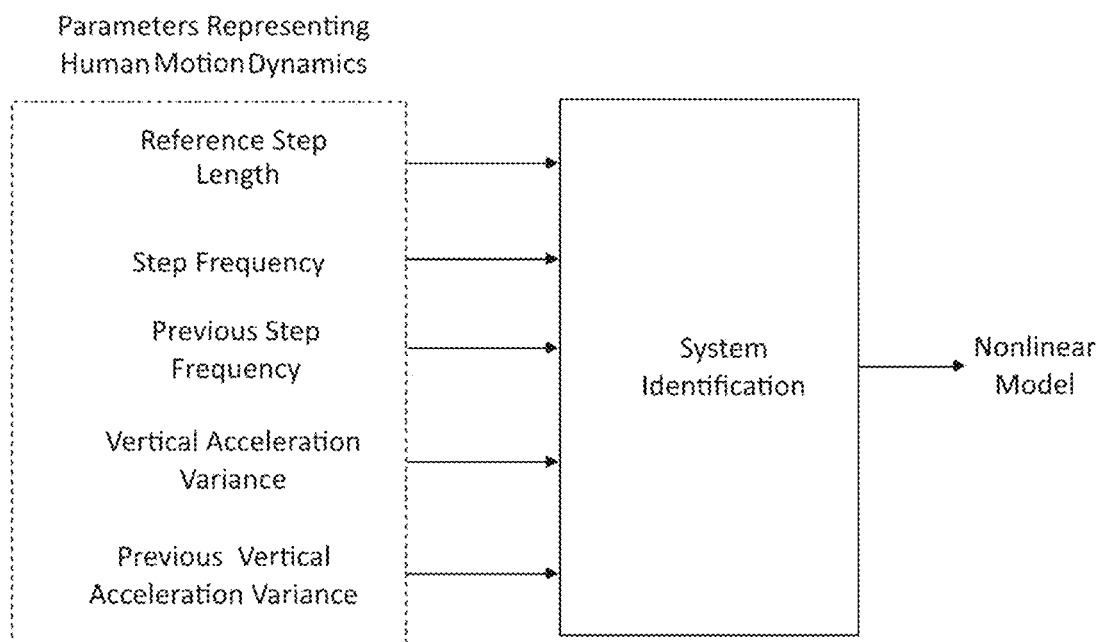
FIG. 9 is a schematic representation of building a nonlinear model to characterize on foot motion according to an embodiment.
Figure 10:
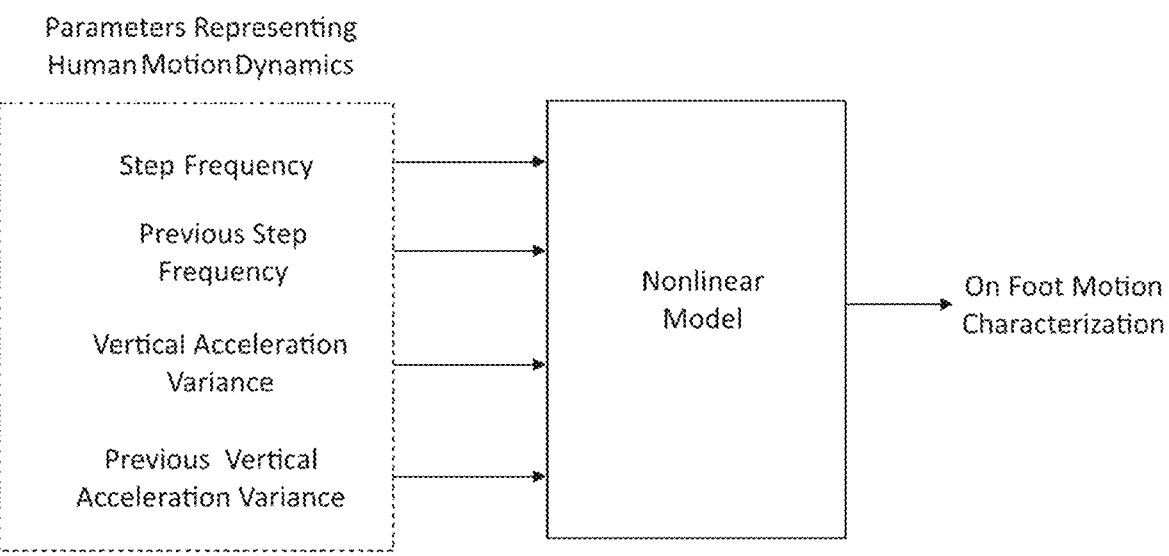
FIG. 10 is a schematic representation of using a nonlinear model to characterize on foot motion according to an embodiment.

An example of the model building phase is schematically depicted in FIG. 9. As shown, parameters representing human motion dynamics are fed to a system identification module to generate a nonlinear model for characterizing on foot motion. In this embodiment, reference step length, step frequency, previous step frequency, vertical acceleration variance and previous vertical acceleration variance are used to generate a model for estimating step length. Second, the derived model may be used in the architectures described above with parameters measured by inertial sensor 112 and/or external sensor 114, or combinations of parameters from multiple sensor assemblies to characterize on foot motion. Correspondingly, an example of the model usage phase is schematically depicted in FIG. 10. Here, parameters representing human motion dynamics are fed to the generated nonlinear model in order to characterize on foot motion. In this embodiment, step frequency, previous step frequency, vertical acceleration variance and previous vertical acceleration variance are used to estimate step length.

Inputs to the model for both the model-building phase and the usage phase may be any suitable parameters that represent human motion dynamics together with other inputs derived from some or all of these parameters. As noted above, each sensor assembly, such as inertial sensor 112 and/or external sensor 114, may measure sufficient parameters to independently characterize on foot motion of the user. Further, different parameters may be used depending on what aspect of on foot motion is being characterized. For example, vertical acceleration or the magnitude of the accelerometer readings may be used to detect steps and in calculating parameters from the acceleration readings during the detected step. Further, parameters that may be used for step length estimation include any combination of step frequency, acceleration variance during step, acceleration peak value during step, peak to peak acceleration value during step and others. In one aspect, different time-delayed versions of these parameters and/or terms obtained by multiplying: (a) any/some/all of these parameters or their time-delayed versions by (b) any/some/all of these parameters or their time-delayed versions may also be employed.

As will be appreciated, the mechanics of on foot motion may vary dependent on a variety of factors, including user activity and device use cases at different applications (such as calling, texting, dangling, or in pocket among others) and different user dynamics due to for example different speeds of travel, different gaits, or due to user physical characteristics. User activity, device use case and/or user dynamics collectively are refereed herein as user motion profile. Rather than building a model intended to cover all possible users' motion profiles, in some embodiments it may be desirable to build multiple models and selectively apply one of the models based on its expected suitability.

For example, in the context of different users' motion profiles due to, for example, different activity or different device use cases at different applications, different models may be built for ranges of different use cases such as handheld, dangling and in pocket. Correspondingly, characterization of on foot motion may then be performed using the appropriate model that corresponds to a detected current user motion profile. In another example, in the context of different users' motion profiles due to, for example, different dynamics at different speeds of locomotion and user physical characteristics, different models may be built for ranges of different user dynamics at different speeds such as fast, medium and slow, and different user physical characteristics such as gender, height and age. Correspondingly, characterization of on foot motion may then be performed using the appropriate model that corresponds to a detected current user motion profile. As will be appreciated, as many models as desired may be constructed and may depend, in part, on the granularity with which a user's current motion profile may be classified.

Figure 11:
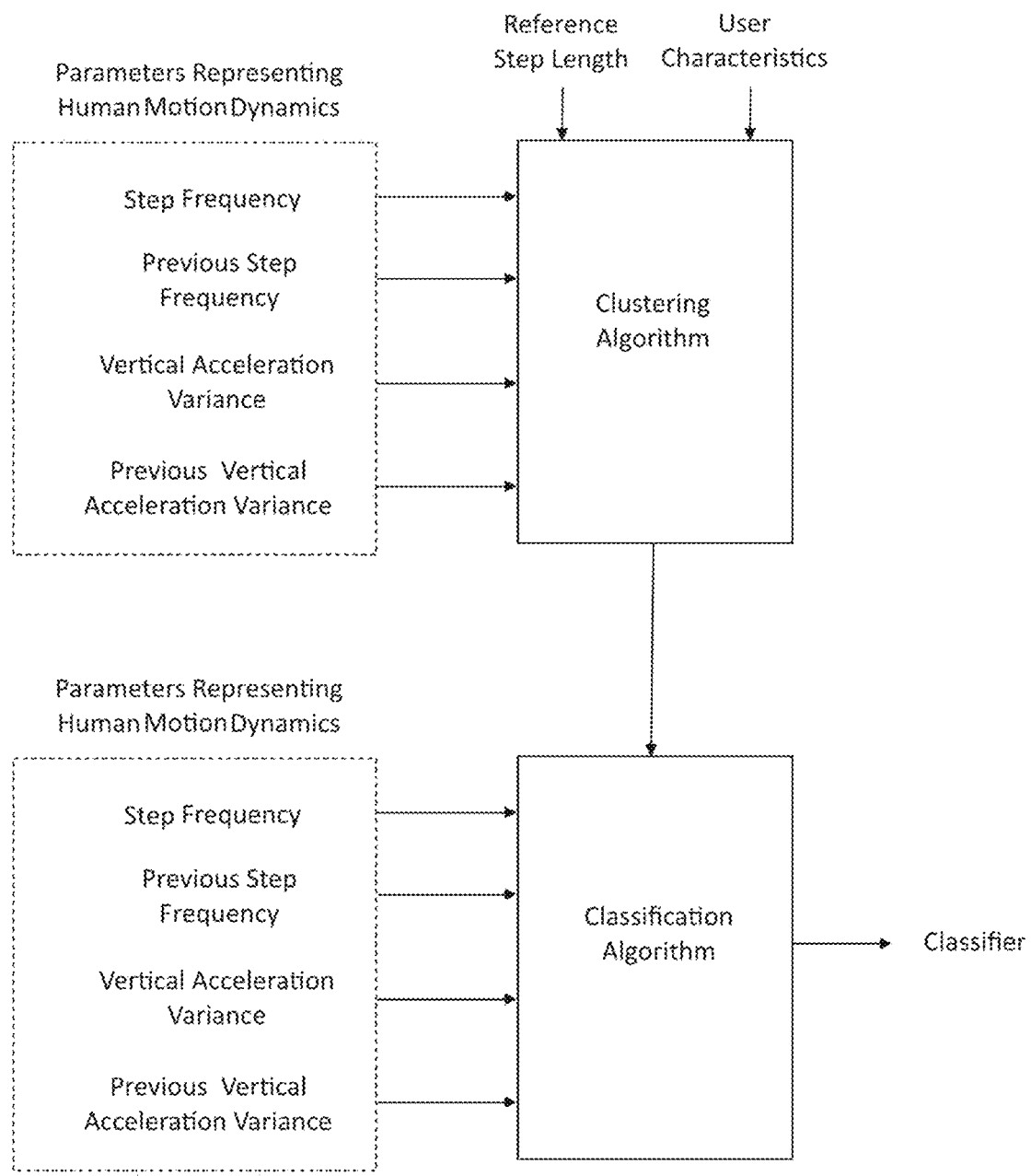
FIG. 11 is a schematic representation of generating a decision tree for classifying a motion profile to characterize on foot motion according to an embodiment.

To help illustrate aspects of such embodiments, FIG. 11 illustrates one suitable method of classifying a user's motion profile employing a classifier. As with model building, inputting to a clustering algorithm, parameters representing human motion dynamics, any reference signal(s), and user characteristics' representative signal(s) whose values are used to group users into subsets according to some criteria such as device use case or user dynamics, this user characteristics signal helps the clustering algorithm to divide the training data into subsets according to users motion profiles. Both the reference signal(s) and user characteristics signal(s) can be available at model building phase only, but do not have to be present at model usage phase. In turn, the outputs of the clustering algorithm may be used to build a classifier using a classification algorithm. The function of the clustering algorithm may be analogized to compressing the information represented by the input parameters so that the decision tree may be trained to decompress this information by using a subset of the input parameter(s) which is available only at the model usage phase to classify the user's motion profile. In one aspect, a suitable clustering algorithm may include a k-means clustering algorithm to assign data into groups based on the means of each group, and a suitable classification algorithm may be a decision tree classification algorithm.

In one embodiment, a clustering algorithm may be applied to the same parameters used to build a model for estimating step length, including current and previous step frequency, current and previous vertical acceleration variance and reference step length. Additionally, a further input whose values are used to group users into subsets according to their motion profiles may be employed. By feeding these inputs to the clustering algorithm, a classification algorithm may be used to generate a classifier that responds to some or all of the inputs to classify the user's motion profile. For example, a classifier such as a decision tree may identify a current class of the user's motion profile dependent on current and previous step frequency and current and previous vertical acceleration variance. Other classifier techniques may be used as desired.

Figure 12:
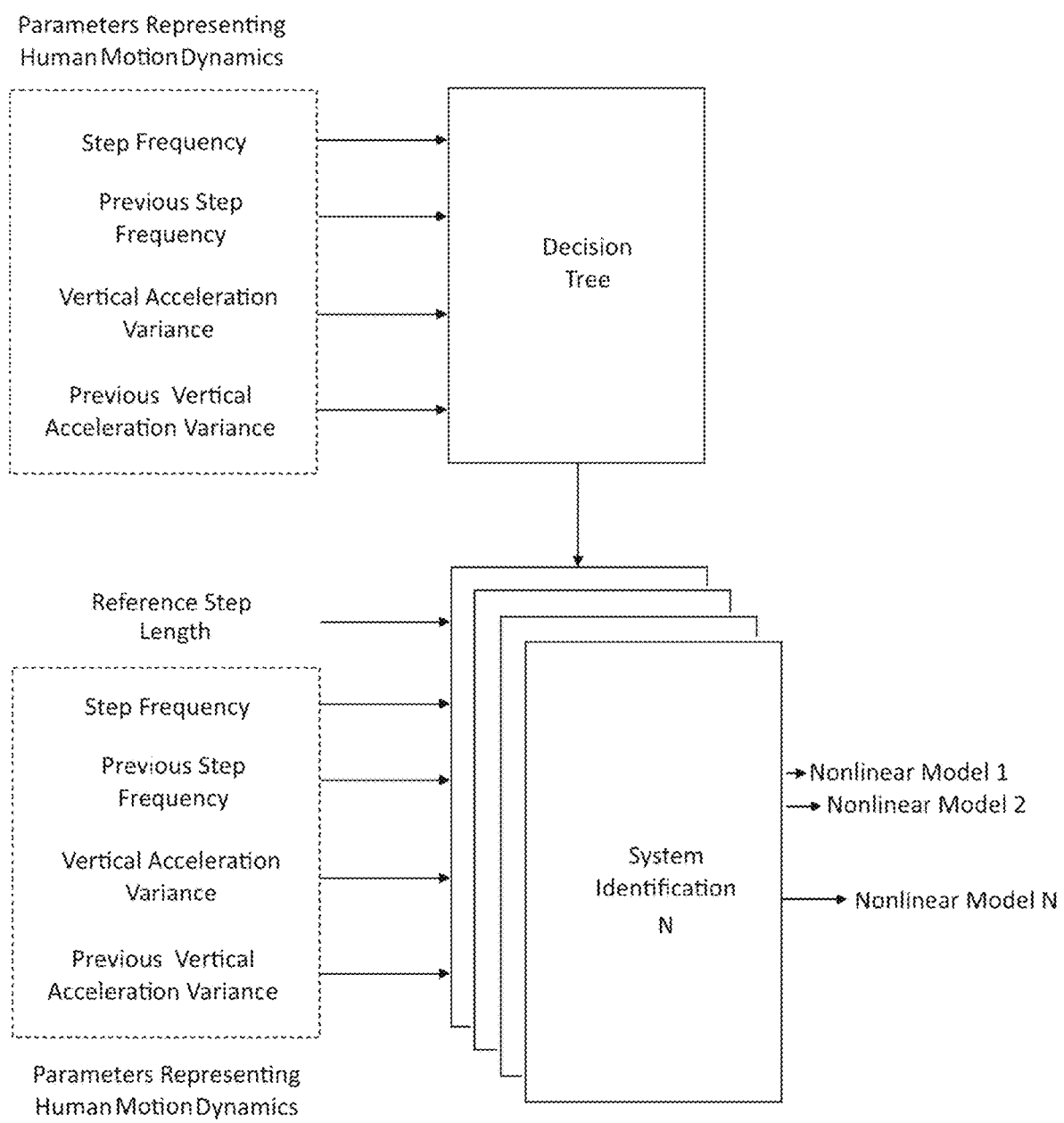
FIG. 12 is a schematic representation of building multiple nonlinear models for different classifications to characterize on foot motion according to an embodiment.
Figure 13:
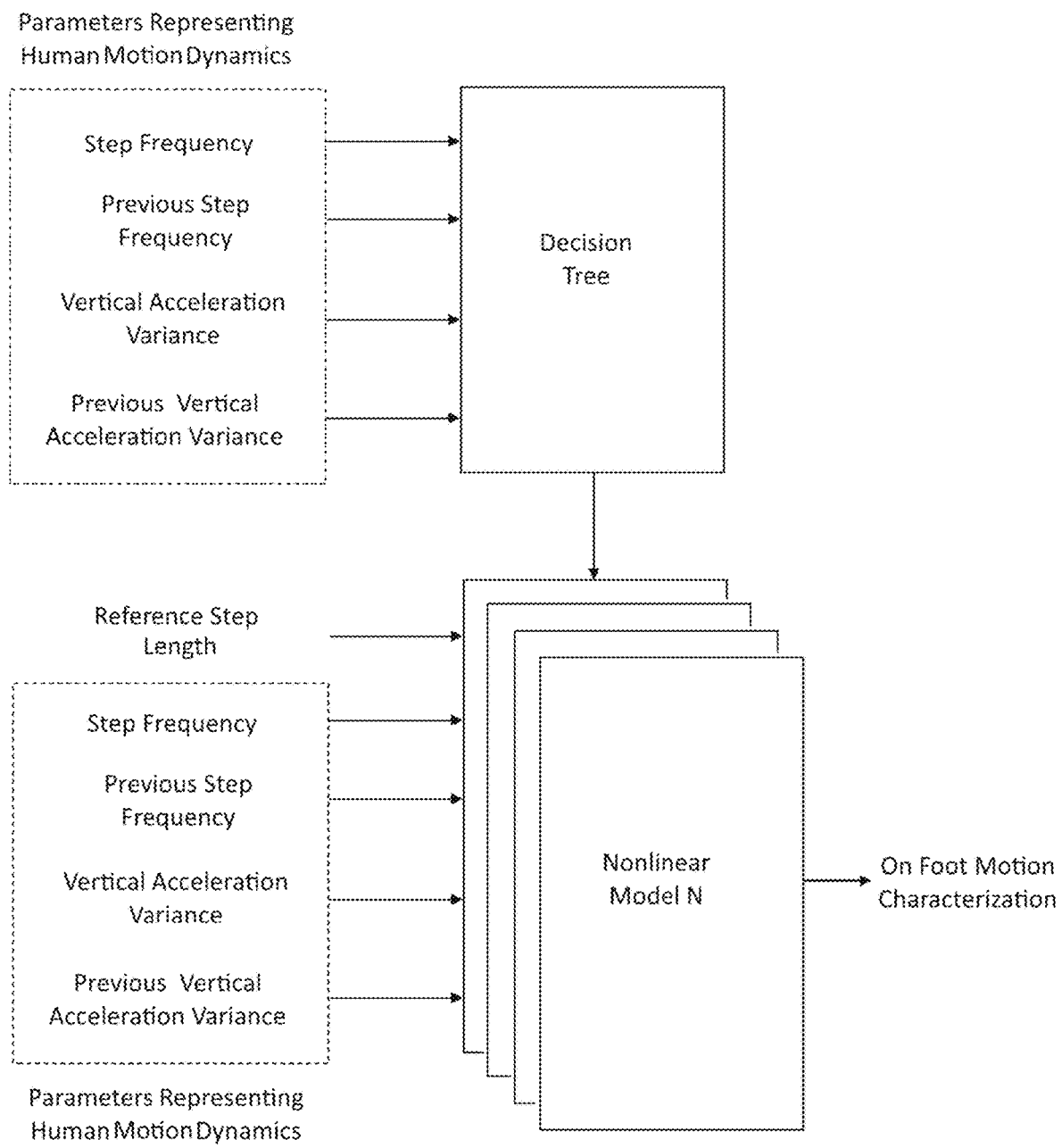
FIG. 13 is a schematic representation of using multiple nonlinear models for different classifications to characterize on foot motion according to an embodiment.

Accordingly, the model building and usage phases described above may be extended to incorporate multiple nonlinear models so that classification of user motion profile may result in selection of an optimized model for the current user and activity/dynamics. For example, FIG. 12 shows that parameters representing human motion dynamics may be used to generate a decision for classifying user motion profile using a decision tree, such as may be generated as described above in reference to FIG. 11. Based on the results of the decision tree, a plurality of distinct user motion profiles N may be identified. In turn, parameters representing human motion dynamics together with additional inputs, such as reference step length, may be used to build N nonlinear models from a corresponding group of system identification routines, System Identification 1, System Identification 2, . . . , System Identification N, in which each model corresponds to a different classified user motion profile. Following model building, the model usage phase may also employ the multiple models according to the classified user motion profile as illustrated in FIG. 13. Depending on the output of the decision tree, an appropriate model may be selected from the group of models, Nonlinear Model 1, Nonlinear Model 2, . . . , Nonlinear Model N, to process the parameters representing human motion dynamics inputs to characterize on foot motion, such as by estimating step length.

A suitable a general-purpose nonlinear system identification technique that may be employed is Fast Orthogonal search (FOS). This technique finds functional expansions using an arbitrary set of non-orthogonal candidate functions. The algorithm may be used for the detection of signals that may be masked by short- and long-term errors. FOS is used in the system identification of a nonlinear system, such as given by the difference model of Equation (1), in which x(n) is the system input, y(n) is the system output, the system error is given by e(n) and n=0, 1, 2, . . . , N where N is the number of samples:

$$y(n)=F[y(n-1), \ldots y(n-K), x(n), \ldots x(n-L)]+e(n) \quad (1)$$

In turn, this may be represented by the summation indicated in Equation (2), in which $a_m$ represents the weights of the non-orthogonal candidate functions, $P_m$ represents the non-orthogonal candidate functions, and M is the number of candidate functions:

$$y(n) = \sum_{m=0}^{M} a_m P_m(n) + e(n) \quad (2)$$

A suitable FOS technique may begin by building a functional expansion of y(n) using a group of orthogonal functions, in which $g_m$ represents the weight of the orthogonal functions and $w_m$ is a set of orthogonal functions derived from $P_m$ by using a Gram-Schmidt (GS) Ortho-normalization process to generate Equation (3):

$$y(n) = \sum_{m=0}^{M} g_m w_m(n) + e(n) \quad (3)$$

GS weights $\alpha_{m,r}$ may be produced by using appropriate GS algorithms and in turn these weights may be used to calculate the orthogonal function $w_m$ according to Equation (4), in which m=1, 2, 3 . . . M and represents the index of the current term and r=0, 1, 2 . . . m−1 and represents the index of the previously term:

$$w_m(n) = P_m(n) - \sum_{r=0}^{m-1} \alpha_{m,r} w_r(n) \quad (4)$$

Accordingly, using FOS to model the nonlinear system may involve calculation of $\alpha_{m,r}$ using the GS method followed by calculation of $g_m$ which is used with output y(n) to find the weight of the non-orthogonal candidate functions $a_m$.

First, the GS weights $\alpha_{m,r}$ may be calculated using Equation (5):

$$\alpha_{mr}(n) = \frac{\overline{P_m(n) * w_r(n)}}{\overline{w_r^2(n)}} \quad (5)$$

The GS weight may be derived without calculating the orthogonal functions $w_m$ using the correlation of the candidate functions and the orthogonal functions D(m,r) according to Equation (6):

$$D(m,r)=\overline{P_m(n)*w_r(n)} \quad (6)$$

In turn, Equation (6) may also be expressed as Equation (7), in which index i=m+1, 2 . . . M:

$$D(m, r) = \overline{P_m(n) * P_r(n)} - \sum_{i=0}^{i-1} \alpha_{r1} D(m, i) \quad (7)$$

As will be appreciated from the above, employing FOS may avoid explicit creation of the orthogonal functions to reduce computing time and storage requirements without degradation of results.

By combining Equations (5) and (6), the weights of GS may be expressed according to Equation (8):

$$\alpha_{mr}(n) = \frac{D(m, r)}{D(r, r)} \quad (8)$$

Further, the orthogonal functions wm may be expressed according to Equation (9):

$$D(m,m) = \overline{w_m^2(n)} \quad (9)$$

Next, following calculation of the Gram Schmidt weights $\alpha_{m,r}$, the orthogonal functions are used to calculate and compute the orthogonal weights $g_m$ with the goal of minimizing the Mean Squared Error (MSE) of the orthogonal functional expansion. The MSE may be given as Equation (10):

$$MSE = \overline{e^2(n)} = \overline{y^2(n)} - \sum_{m=0}^{M} g_m^2 * \overline{w_m^2(n)} \quad (10)$$

By deriving Equation (10) with respect to the $g_m$ and setting its value to zero, the value of the orthogonal weights which minimize the value of the MSE may be given as in Equation (11):

$$g_m = \frac{\overline{y(n) * w_m(n)}}{\overline{w_m^2(n)}} \quad (11)$$

To calculate $g_m$ as indicated by Equation (11), the mean average value of the output and the orthogonal functions may be used as given in Equation (12), in which C(m) may be solved recursively by setting C(0) equal to the mean square average of the output y(n) for m=1, 2, 3 . . . M:

$$C(m) = \overline{y(n) * w_m(n)} = \overline{P_m(n) * y(n)} - \sum_{r=0}^{m-1} \alpha_{mr} * C(r) \quad (12)$$

Correspondingly, the value of the orthogonal weights $g_m$ may be expressed as Equation (13):

$$g_m = \frac{C(m)}{D(m, m)} \quad (13)$$

The MSE reduction from the addition of the $m^{th}$ term may be represented by Equation (14), in which the candidate with the largest value for Q is selected as the model term, but optionally, its addition to the model may be subject to its Q value exceeding a threshold level:

$$Q(M) = g_m^2 * \overline{w_m^2(n)} = g_m^2 * D(M,M) \quad (14)$$

After obtaining the orthogonal weights $g_m$ and the GS weights $\alpha_{m,r}$, the coefficients $a_m$ of Equation (2) may be calculated from Equation (15), in which $v_i$ is given by Equation (16):

$$a_m = \sum_{i=m}^{M} g_i * v_i \quad (15)$$

$$v_i = -\sum_{r=m}^{i-1} \alpha_{ir} * v_r \text{ and } v_m = 1 \quad (16)$$

Thus, calculation of coefficients $a_m$ and selection of model terms $P_m(n)$ provides a suitable representation of Equation (2) for use in estimating step length.

Use of the FOS techniques described above allows selection of the candidate functions representing the system together along with obtaining the associated coefficients, in contrast to techniques that provide coefficients only for known model structures. As will be appreciated, FOS is an efficient and effective method of system identification that is able to find accurate models of systems even from very large numbers of candidate basis functions. Further, FOS techniques may select candidates from an over-complete set given the ability to choose the most significant candidates.

Further, the speed associated with FOS techniques allows for dynamic training during use of device 100 and customization to parameters associated with an individual user. For example, selection among multiple step length models allows dynamic training when reference information is available, such as a satellite navigation solution. In another aspect, dynamic training and personal identification may be automatically enabled using step parameters for user identification. For example, when the same user is identified more than a predefined threshold of number of times, training mode may be enabled to customize the step length estimation to the user and when another user (guest) is identified, a default model may be used.

Accordingly, suitable implementations of a FOS algorithm may be employed to build a varying step length nonlinear model as noted above. During model-building, a reference step length and the parameters representing human motion dynamics are collected, stored and then fed to the FOS model with each step detected. Additionally, multiple FOS models may be built to correspond to different classifications of user activity or dynamics as also described above.

Certain advantages associated with the techniques of this disclosure may be appreciated in the context of a test scenario comparing characterizations of on foot motion using a single sensor assembly to characterizations made by synthesizing multiple sensor assemblies. Sample trajectories were obtained from 16 different test users, each employing multiple sensor assemblies. In this example, three sensor assemblies were used in the form of three separate devices, a phone, a watch and glasses. The trajectories were obtained for each test user at three different walking speeds—slow, normal and fast, by walking in a straight line to a predetermined location, turning around and returning to the start. Furthermore, several data sets were generated for each test user in each speed category for verification, representing different usage orientations for the respective devices, including handheld/viewing mode, dangling and pocket for the watch and phone. Different physical characteristics were factored into the nonlinear model used to estimate step length, including height, weight, gender and age. The results from the test users were collated into a dataset representing 240 trajectories and the results are summarized in Table 1.

TABLE 1

| Device | Mean Enhancement Per Device % |
| --- | --- |
| Phone | 22.81% |
| Watch | 17.97% |
| Glasses | 9.43% |

As will be appreciated, the characterization of on foot motion determined from multiple sensor assemblies exhibits increased accuracy in relation to characterizations determined from a single sensor assembly. In this test, greater improvement was achieved in comparison to a single sensor assembly in devices having a more freedom of orientation, the watch and phone, than in the device having a more constrained orientation, the glasses.

Figure 14:
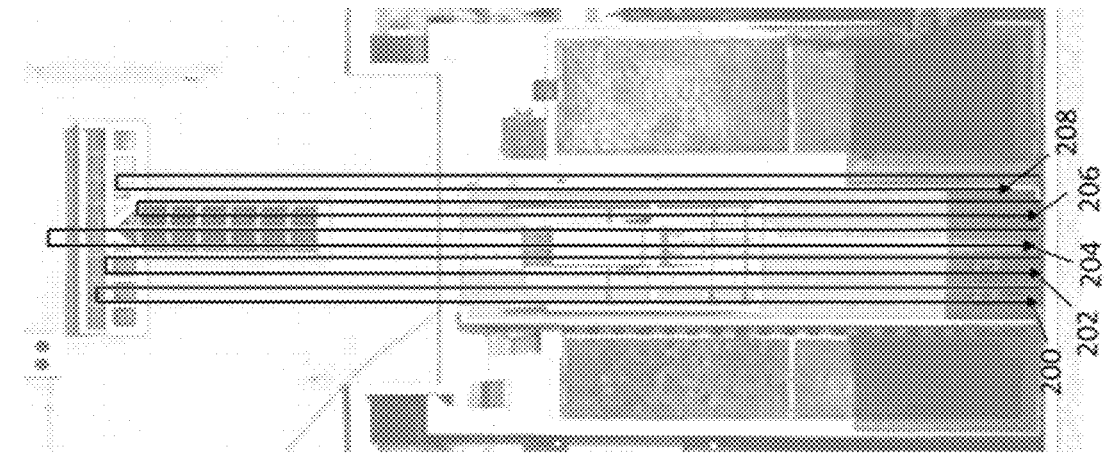
FIG. 14 is a schematic representation of a test at slow walking speed of characterizing on foot motion according to an embodiment.
Figure 15:
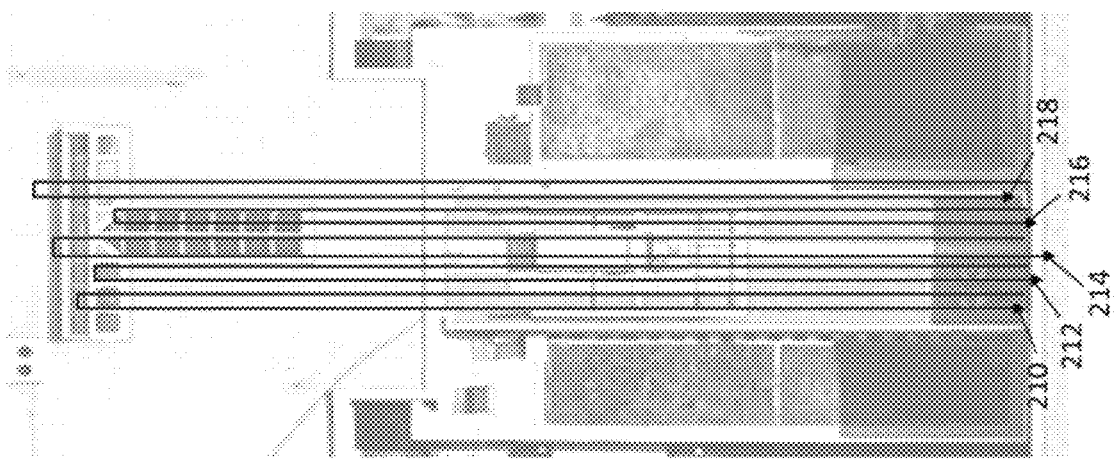
FIG. 15 is a schematic representation of a test at normal walking speed of characterizing on foot motion according to an embodiment.
Figure 16:
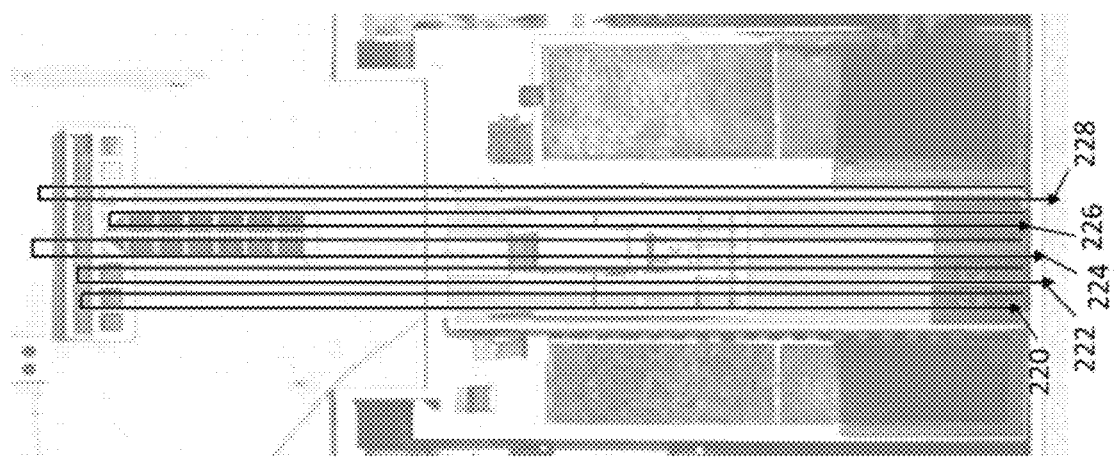
FIG. 16 is a schematic representation of a test at fast walking speed of characterizing on foot motion according to an embodiment.

The relative improvements observed from the use of multiple sensor assemblies are graphically represented in FIGS. 14-16 with respect to a reference route within a building, showing the results obtained from the glasses, the watch in viewing orientation and the phone when dangling. The slow speed trajectories are shown in FIG. 14, with trace 200 representing the reference, trace 202 representing the trajectory derived from characterizing on foot motion with multiple sensor assemblies, trace 204 representing the trajectory derived from characterizing on foot motion with the sensor assembly of the phone, trace 206 representing the trajectory derived from characterizing on foot motion with the sensor assembly of the watch and trace 208 representing the trajectory derived from characterizing on foot motion with the sensor assembly of the glasses. Next, the normal speed trajectories are shown in FIG. 15, with trace 210 representing the reference, trace 212 representing the trajectory derived from characterizing on foot motion with multiple sensor assemblies, trace 214 representing the trajectory derived from characterizing on foot motion with the sensor assembly of the phone, trace 216 representing the trajectory derived from characterizing on foot motion with the sensor assembly of the watch and trace 218 representing the trajectory derived from characterizing on foot motion with the sensor assembly of the glasses. Finally, the fast speed trajectories are shown in FIG. 16, with trace 220 representing the reference, trace 222 representing the trajectory derived from characterizing on foot motion with multiple sensor assemblies, trace 224 representing the trajectory derived from characterizing on foot motion with the sensor assembly of the phone, trace 226 representing the trajectory derived from characterizing on foot motion with the sensor assembly of the watch and trace 228 representing the trajectory derived from characterizing on foot motion with the sensor assembly of the glasses.

Depending on the architecture of device 100, sensor processor 108 and inertial sensor 112 may be formed on different chips, or as shown, may reside on the same chip. A sensor fusion algorithm employed to calculate the orientation of device 100 may be performed externally to sensor processor 108 and MPU 106, such as by host processor 104, or may be performed by MPU 106. A chip may be defined to include at least one substrate typically formed from a semiconductor material. A single chip may be formed from multiple substrates, where the substrates are mechanically bonded to preserve the functionality. A multiple chip includes at least two substrates, wherein the two substrates are electrically connected, but do not require mechanical bonding. A package provides electrical connection between the bond pads on the chip to a metal lead that can be soldered to a PCB. A package typically comprises a substrate and a cover. Integrated Circuit (IC) substrate may refer to a silicon substrate with electrical circuits, typically CMOS circuits. One or more sensors may be incorporated into the package if desired using any suitable technique. In some embodiments, a sensor may be MEMS-based, such that a MEMS cap provides mechanical support for the MEMS structure. The MEMS structural layer is attached to the MEMS cap. The MEMS cap is also referred to as handle substrate or handle wafer. In some embodiments, the first substrate may be vertically stacked, attached and electrically connected to the second substrate in a single semiconductor chip, while in other embodiments, the first substrate may be disposed laterally and electrically connected to the second substrate in a single semiconductor package. In one embodiment, the first substrate is attached to the second substrate through wafer bonding, as described in commonly owned U.S. Pat. No. 7,104,129, which is incorporated herein by reference in its entirety, to simultaneously provide electrical connections and hermetically seal the MEMS devices. This fabrication technique advantageously enables technology that allows for the design and manufacture of high performance, multi-axis, inertial sensors in a very small and economical package. Integration at the wafer-level minimizes parasitic capacitances, allowing for improved signal-to-noise relative to a discrete solution. Such integration at the wafer-level also enables the incorporation of a rich feature set which minimizes the need for external amplification.

The techniques of this disclosure may be combined with any navigation solution independent of the type of the state estimation or filtering technique used in this navigation solution. The state estimation technique can be linear, nonlinear or a combination thereof. Different examples of techniques used in the navigation solution may rely on a Kalman filter, an Extended Kalman filter, a non-linear filter such as a particle filter, or an artificial intelligence technique such as Neural Network or Fuzzy systems. The state estimation technique used in the navigation solution can use any type of system and/or measurement models. The navigation solution may follow any scheme for integrating the different sensors and systems, such as for example loosely coupled integration scheme or tightly coupled integration scheme among others. The navigation solution may utilize modeling (whether with linear or nonlinear, short memory length or long memory length) and/or automatic calibration for the errors of inertial sensors and/or the other sensors used.

CONTEMPLATED EMBODIMENTS

The present disclosure describes the body frame to be x forward, y positive towards right side of the body and z axis positive downwards. It is contemplated that any body-frame definition can be used for the application of the method and apparatus described herein.

It is contemplated that the techniques of this disclosure can be used with a navigation solution that may optionally utilize automatic zero velocity periods or static period detection with its possible updates and inertial sensors bias recalculations, non-holonomic updates module, advanced modeling and/or calibration of inertial sensors errors, derivation of possible measurements updates for them from GNSS when appropriate, automatic assessment of GNSS solution quality and detecting degraded performance, automatic switching between loosely and tightly coupled integration schemes, assessment of each visible GNSS satellite when in tightly coupled mode, and finally possibly can be used with a backward smoothing module with any type of backward smoothing technique and either running in post mission or in the background on buffered data within the same mission.

It is further contemplated that techniques of this disclosure can also be used with a mode of conveyance technique or a motion model detection technique to establish the mode of conveyance. This enables the detection of pedestrian mode among other modes such as for example driving mode. When pedestrian mode is detected, the method presented in this disclosure can be made operational to determine the misalignment between the device and the pedestrian.

It is further contemplated that techniques of this disclosure can also be used with a navigation solution that is further programmed to run, in the background, a routine to simulate artificial outages in the absolute navigational information and estimate the parameters of another instance of the state estimation technique used for the solution in the present navigation module to optimize the accuracy and the consistency of the solution. The accuracy and consistency is assessed by comparing the temporary background solution during the simulated outages to a reference solution. The reference solution may be one of the following examples: the absolute navigational information (e.g. GNSS); the forward integrated navigation solution in the device integrating the available sensors with the absolute navigational information (e.g. GNSS) and possibly with the optional speed or velocity readings; or a backward smoothed integrated navigation solution integrating the available sensors with the absolute navigational information (e.g. GNSS) and possibly with the optional speed or velocity readings. The background processing can run either on the same processor as the forward solution processing or on another processor that can communicate with the first processor and can read the saved data from a shared location. The outcome of the background processing solution can benefit the real-time navigation solution in its future run (i.e. real-time run after the background routine has finished running), for example, by having improved values for the parameters of the forward state estimation technique used for navigation in the present module.

It is further contemplated that the techniques of this disclosure can also be used with a navigation solution that is further integrated with maps (such as street maps, indoor maps or models, or any other environment map or model in cases of applications that have such maps or models available), and a map matching or model matching routine. Map matching or model matching can further enhance the navigation solution during the absolute navigation information (such as GNSS) degradation or interruption. In the case of model matching, a sensor or a group of sensors that acquire information about the environment can be used such as, for example, Laser range finders, cameras and vision systems, or sonar systems. These new systems can be used either as an extra help to enhance the accuracy of the navigation solution during the absolute navigation information problems (degradation or absence), or they can totally replace the absolute navigation information in some applications.

It is further contemplated that the techniques of this disclosure can also be used with a navigation solution that, when working either in a tightly coupled scheme or a hybrid loosely/tightly coupled option, need not be bound to utilize pseudorange measurements (which are calculated from the code not the carrier phase, thus they are called code-based pseudoranges) and the Doppler measurements (used to get the pseudorange rates). The carrier phase measurement of the GNSS receiver can be used as well, for example: (i) as an alternate way to calculate ranges instead of the code-based pseudoranges, or (ii) to enhance the range calculation by incorporating information from both code-based pseudorange and carrier-phase measurements; such enhancement is the carrier-smoothed pseudorange.

It is further contemplated that the techniques of this disclosure can also be used with a navigation solution that relies on an ultra-tight integration scheme between GNSS receiver and the other sensors' readings.

It is further contemplated that the techniques of this disclosure can also be used with a navigation solution that uses various wireless communication systems that can also be used for positioning and navigation either as an additional aid (which will be more beneficial when GNSS is unavailable) or as a substitute for the GNSS information (e.g. for applications where GNSS is not applicable). Examples of these wireless communication systems used for positioning are, such as, those provided by cellular phone towers and signals, radio signals, digital television signals, WiFi, or WiMax. For example, for cellular phone based applications, an absolute coordinate from cell phone towers and the ranges between the indoor user and the towers may be utilized for positioning, whereby the range might be estimated by different methods among which calculating the time of arrival or the time difference of arrival of the closest cell phone positioning coordinates. A method known as Enhanced Observed Time Difference (E-OTD) can be used to get the known coordinates and range. The standard deviation for the range measurements may depend upon the type of oscillator used in the cell phone, and cell tower timing equipment and the transmission losses. WiFi positioning can be done in a variety of ways that includes but is not limited to time of arrival, time difference of arrival, angles of arrival, received signal strength, and fingerprinting techniques, among others; all of the methods provide different level of accuracies. The wireless communication system used for positioning may use different techniques for modeling the errors in the ranging, angles, or signal strength from wireless signals, and may use different multipath mitigation techniques. All the above mentioned ideas, among others, are also applicable in a similar manner for other wireless positioning techniques based on wireless communications systems.

It is further contemplated that the techniques of this disclosure can also be used with a navigation solution that utilizes aiding information from other moving devices. This aiding information can be used as additional aid (that will be more beneficial when GNSS is unavailable) or as a substitute for the GNSS information (e.g. for applications where GNSS based positioning is not applicable). One example of aiding information from other devices may be relying on wireless communication systems between different devices. The underlying idea is that the devices that have better positioning or navigation solution (for example having GNSS with good availability and accuracy) can help the devices with degraded or unavailable GNSS to get an improved positioning or navigation solution. This help relies on the well-known position of the aiding device(s) and the wireless communication system for positioning the device(s) with degraded or unavailable GNSS. This contemplated variant refers to the one or both circumstance(s) where: (i) the device(s) with degraded or unavailable GNSS utilize the methods described herein and get aiding from other devices and communication system, (ii) the aiding device with GNSS available and thus a good navigation solution utilize the methods described herein. The wireless communication system used for positioning may rely on different communication protocols, and it may rely on different methods, such as for example, time of arrival, time difference of arrival, angles of arrival, and received signal strength, among others. The wireless communication system used for positioning may use different techniques for modeling the errors in the ranging and/or angles from wireless signals, and may use different multipath mitigation techniques.

The embodiments and techniques described above may be implemented in software as various interconnected functional blocks or distinct software modules. This is not necessary, however, and there may be cases where these functional blocks or modules are equivalently aggregated into a single logic device, program or operation with unclear boundaries. In any event, the functional blocks and software modules implementing the embodiments described above, or features of the interface can be implemented by themselves, or in combination with other operations in either hardware or software, either within the device entirely, or in conjunction with the device and other processor enabled devices in communication with the device, such as a server.

Although a few embodiments have been shown and described, it will be appreciated by those skilled in the art that various changes and modifications can be made to these embodiments without changing or departing from their scope, intent or functionality. The terms and expressions used in the preceding specification have been used herein as terms of description and not of limitation, and there is no intention in the use of such terms and expressions of excluding equivalents of the features shown and described or portions thereof, it being recognized that the disclosure is defined and limited only by the claims that follow.

What is claimed is:

1. A method for quantifying on foot motion of a user with a portable device comprising:
   obtaining parameters to quantify the on foot motion of the user based on sensor data from a first sensor assembly integrated with the portable device such that on foot motion of the user results in a corresponding motion of the first sensor assembly;
   obtaining parameters to quantify the on foot motion of the user based on sensor data from at least one additional sensor assembly integrated with a portable device such that on foot motion of the user results in a corresponding motion of each additional sensor assembly, wherein each additional sensor assembly is independent of the first sensor assembly, wherein each sensor assembly of the first sensor assembly and the at least one additional sensor assembly comprises at least one sensor of the same type, wherein sensors of the same type measure the same quantity, and wherein the sensor assemblies do not have a sensor in common;
   synthesizing the parameters obtained from the first sensor assembly and the parameters obtained from each additional sensor assembly;
   performing an enhanced contemporaneous quantification of the on foot motion of the user by using at least one synthesized parameter from each of the sensor assemblies, wherein enhanced contemporaneous quantification of the on foot motion of the user is by at least one of: i) detecting a step, and ii) estimating step length; and
   outputting the enhanced contemporaneous quantification of the on foot motion.

2. The method of claim 1, wherein quantifying the on foot motion of the user comprises detecting a step.

3. The method of claim 2, wherein quantifying the on foot motion of the user comprises:
   determining whether a step has occurred for each sensor assembly, using at least one parameter obtained from each sensor assembly in making the determination for that sensor assembly; and
   detecting a step by comparing the determinations for each sensor assembly.

4. The method of claim 3, wherein comparing the determinations comprises detecting a step when a number of determinations detecting a step exceed a number of determinations not detecting a step.

5. The method of claim 3, wherein comparing the determinations comprises weighting at least one of the determinations.

6. The method of claim 2, quantifying the on foot motion of the user further comprises estimating step length.

7. The method of claim 1, wherein quantifying the on foot motion of the user comprises estimating step length.

8. The method of claim 7, wherein synthesizing the parameters obtained from the first sensor assembly and the parameters obtained from each additional sensor assembly comprises:
   quantifying the on foot motion of the user with the parameters from the first sensor assembly;
   for each additional sensor assembly, quantifying the on foot motion of the user with the parameters from each additional sensor assembly; and
   combining each quantification.

9. The method of claim 8, wherein the combining comprises an averaging operation.

10. The method of claim 9, wherein the averaging operation comprises weighted averaging.

11. The method of claim 10, wherein the averaging operation comprises dynamically adjusting a weight of at least one factor used in the averaging operation.

12. The method of claim 10, wherein the averaging operation involves scoring.

13. The method of claim 7, wherein synthesizing the parameters obtained from the first sensor assembly and the parameters obtained from each additional sensor assembly comprises generating a combined parameter from at least one parameter obtained from one sensor assembly and at least one corresponding parameter obtained from another sensor assembly prior to quantifying the on foot motion using the combined parameter.

14. The method of claim 13, wherein synthesizing the parameters obtained from the first sensor assembly and the parameters obtained from each additional sensor assembly comprises:
   generating combined parameters for each of the parameters obtained from the first sensor assembly with each of the corresponding parameters obtained from at least one additional sensor assembly; and
   quantifying the on foot motion of the user with the combined parameters.

15. The method of claim 14, wherein the combining comprises an averaging operation.

16. The method of claim 15, wherein the averaging operation comprises weighted averaging.

17. The method of claim 16, wherein the averaging operation comprises dynamically adjusting a weight of at least one factor used in the averaging operation.

18. The method of claim 16, wherein the averaging operation involves scoring.

19. The method of claim 13, further comprising:
   quantifying the on foot motion of the user with the combined parameter and at least one parameter from one of the sensor assemblies;

quantifying the on foot motion of the user with at least one parameter from another of the sensor assemblies; and combining each quantification.

20. The method of claim 19, wherein the combining comprises an averaging operation.

21. The method of claim 20, wherein the averaging operation comprises weighted averaging.

22. The method of claim 21, wherein the averaging operation comprises dynamically adjusting a weight of at least one factor used in the averaging operation.

23. The method of claim 21, wherein the averaging operation involves scoring.

24. The method of claim 13, wherein the combining comprises an averaging operation.

25. The method of claim 24, wherein the averaging operation comprises weighted averaging.

26. The method of claim 25, wherein the averaging operation comprises dynamically adjusting a weight of at least one factor used in the averaging operation.

27. The method of claim 25, wherein the averaging operation involves scoring.

28. The method of claim 7, wherein synthesizing the parameters obtained from the first sensor assembly and the parameters obtained from each additional sensor assembly comprises:
collecting the parameters from the first sensor assembly and the parameters from each additional sensor assembly; and
quantifying the on foot motion of the user with the collected parameters.

29. The method of claim 7, wherein characterizing the on foot motion of the user employs a nonlinear model.

30. The method of claim 29, wherein the nonlinear model is generated by performing a fast orthogonal search.

31. The method of claim 30, wherein performing a fast orthogonal search operation comprises building at least one model for estimating step length using parameters corresponding to the parameters obtained from the first sensor assembly and obtained from each additional sensor assembly.

32. The method of claim 31, wherein performing a fast orthogonal search operations comprises building a plurality of models quantifying the on foot motion of the user.

33. The method of claim 32, further comprising classifying an activity of the user and selecting among the plurality of models based, at least in part, on the classification.

34. The method of claim 32, further comprising classifying dynamics of the user and selecting among the plurality of models based, at least in part, on the classification.

35. The method of claim 30, wherein quantifying the on foot motion of the user comprises feeding the parameters obtained from the first sensor assembly and obtained from each additional sensor assembly to the at least one model to estimate step length.

36. The method of claim 35, wherein quantifying the on foot motion of the user comprises feeding the parameters obtained from the first sensor assembly and obtained from each additional sensor assembly to at least one model selected from a plurality of models to estimate step length.

37. The method of claim 36, further comprising classifying an activity of the user and selecting among the plurality of models based, at least in part, on the classification.

38. The method of claim 36, further comprising classifying dynamics of the user and selecting among the plurality of models based, at least in part, on the classification.

39. A portable device for quantifying on foot motion of a user comprising:
a first sensor assembly integrated with the portable device such that on foot motion of the user results in a corresponding motion of the first sensor assembly, configured to output parameters to quantify the on foot motion of the user;
at least one additional sensor assembly integrated with a portable device such that on foot motion of the user results in a corresponding motion of each additional sensor assembly and communicably coupled to the portable device, wherein each additional sensor assembly is configured to output parameters to quantify the on foot motion of the user and is independent of the first sensor assembly, wherein each sensor assembly of the first sensor assembly and the at least one additional sensor assembly comprises at least one sensor of the same type, wherein sensors of the same type measure the same quantity, and wherein the sensor assemblies do not have a sensor in common; and
a step controller configured to:
a) synthesize the parameters output by the first sensor assembly and the parameters output by each additional sensor assembly,
b) perform an enhanced contemporaneous quantification of the on foot motion of the user, using at least one synthesized parameter from each of the sensor assemblies, wherein enhanced contemporaneous quantification of the on foot motion of the user is by at least one of: i) detecting a step, and ii) estimating step length, and
c) output the enhanced contemporaneous quantification of the on foot motion.

40. The device of claim 39, wherein quantifying the on foot motion of the user comprises detecting steps.

41. The device of claim 39, wherein quantifying the on foot motion of the user comprises estimating varying step length.

42. The device of claim 39, wherein the at least one additional sensor assembly is integrated into the portable device.

43. The device of claim 39, wherein the at least one additional sensor assembly is integrated into another portable device.

44. The device of claim 43, wherein the other portable device is configured as a wearable device.

45. The device of claim 43, wherein the portable device further comprises a communications module configured to communicate with the other portable device.

46. The device of claim 39, wherein the portable device is configured as a wearable device.

47. The device of claim 39, wherein the first sensor assembly comprises an inertial sensor implemented as a Micro Electro Mechanical System (MEMS).

48. A system for quantifying on foot motion of a user comprising:
a first sensor assembly integrated with a first portable device such that on foot motion of the user results in a corresponding motion of the first sensor assembly, configured to output parameters to quantify the on foot motion of the user;
at least one additional sensor assembly integrated with a second portable device such that on foot motion of the user results in a corresponding motion of the at least one additional sensor assembly, wherein each additional sensor assembly is configured to output parameters to quantify the on foot motion of the user and is independent of the first sensor assembly, wherein each sensor assembly of the first sensor assembly and the at least one additional sensor assembly comprises at least one sensor of the same type, wherein sensors of the same type measure the same quantity wherein the first portable device is communicably coupled with the second portable device, and wherein the sensor assemblies do not have a sensor in common; and a step controller implemented in at least one of the first portable device or the second portable device configured to:
  a) synthesize the parameters output by the first sensor assembly and the parameters output by each additional sensor assembly,
  b) perform an enhanced contemporaneous quantification of the on foot motion of the user, using at least one synthesized parameter from each of the sensor assemblies, wherein enhanced contemporaneous quantification of the on foot motion of the use is by at least one of: i) detecting a step, and ii) estimating step length, and
  c) output the enhanced contemporaneous quantification of the on foot motion.

\* \* \* \* \*